US012805882B2

(12) United States Patent
Collazo

(10) Patent No.: US 12,805,882 B2
(45) Date of Patent: Nov. 24, 2026

(54) PATELLA RESECTION GUIDE WITH INDEPENDENT ADJUSTMENT

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

(*) Notice: Subject to any disclaimer, the term of this patent is extended or adjusted under 35 U.S.C. 154(b) by 0 days.

(21) Appl. No.: 19/079,540

(22) Filed: Mar. 14, 2025

(65) Prior Publication Data

US 2025/0213256 A1 Jul. 3, 2025

Related U.S. Application Data

(63) Continuation of application No. 18/212,243, filed on Jun. 21, 2023, now Pat. No. 12,274,457, which is a continuation of application No. 17/495,269, filed on Oct. 6, 2021, now Pat. No. 11,723,677.

(60) Provisional application No. 63/092,675, filed on Oct. 16, 2020.

(51) Int. Cl.

| | |
|---|---|
| ***A61B 17/17*** | (2006.01) |
| ***A61B 17/15*** | (2006.01) |
| *A61B 90/00* | (2016.01) |

(52) U.S. Cl.
CPC ........ *A61B 17/1767* (2013.01); *A61B 17/158* (2013.01); *A61B 2090/3983* (2016.02)

(58) Field of Classification Search
CPC . A61B 7/158; A61B 17/1677; A61B 17/1767; A61B 17/158
See application file for complete search history.

(56) References Cited

U.S. PATENT DOCUMENTS

| | | | |
|---|---|---|---|
| 2,181,746 | A | 11/1939 | Siebrandt |
| 5,021,055 | A | 6/1991 | Burkinshaw et al. |
| 5,129,907 | A | 7/1992 | Heldreth et al. |
| 5,147,365 | A | 9/1992 | Whitlock et al. |
| 5,542,947 | A | 8/1996 | Treacy |
| 6,010,509 | A | 1/2000 | Delgado et al. |
| 7,566,335 | B1 | 7/2009 | Scott et al. |
| 7,632,279 | B2 | 12/2009 | Bastian |
| 8,728,087 | B2 | 5/2014 | Soliman et al. |
| 8,821,501 | B2 | 9/2014 | Kecman et al. |
| 8,915,923 | B2 | 12/2014 | Vail et al. |
| 8,968,321 | B2 | 3/2015 | Wright et al. |
| 8,979,854 | B2 | 3/2015 | Wright et al. |
| 8,986,306 | B2 | 3/2015 | Wright et al. |
| 8,998,912 | B2 | 4/2015 | Spencer Jones et al. |
| 8,998,913 | B2 | 4/2015 | Choong et al. |

(Continued)

FOREIGN PATENT DOCUMENTS

| | | | |
|---|---|---|---|
| EP | 0327249 | A2 | 8/1989 |
| EP | 2540239 | A1 | 1/2013 |
| EP | 3072462 | B1 | 10/2017 |

*Primary Examiner* — Matthew J Lawson
(74) *Attorney, Agent, or Firm* — Lerner David LLP

(57) ABSTRACT

A patellar resection guide includes a frame, a first jaw, and a second jaw. The frame includes a first end, at which the first jaw is disposed, and a second end opposed to the first end at which the second jaw is disposed. The guide further includes an arm with a planar surface for guiding a cutting tool. The arm is either or both of rotatable and translatable relative to the frame.

20 Claims, 22 Drawing Sheets

(56) References Cited

U.S. PATENT DOCUMENTS

| | | | | |
|---|---|---|---|---|
| 9,078,676 | B2 | 7/2015 | Randle et al. | |
| 9,078,772 | B2 | 7/2015 | Jones et al. | |
| 9,414,851 | B2 | 8/2016 | Kecman et al. | |
| 9,554,813 | B2 | 1/2017 | Clever et al. | |
| 9,750,515 | B2 | 9/2017 | Soliman et al. | |
| 10,076,345 | B2 | 9/2018 | Harris et al. | |
| 10,085,758 | B2 | 10/2018 | Wallace et al. | |
| 10,314,599 | B2 | 6/2019 | Hampp et al. | |
| 10,588,639 | B2 | 3/2020 | Fraone et al. | |
| 2004/0153066 | A1 | 8/2004 | Coon et al. | |
| 2006/0052792 | A1* | 3/2006 | Boettiger | A61B 90/39 606/88 |
| 2006/0142777 | A1 | 6/2006 | Bastian | |
| 2007/0162142 | A1* | 7/2007 | Stone | A61B 34/20 623/20.14 |
| 2008/0097450 | A1 | 4/2008 | Brown et al. | |
| 2009/0183740 | A1* | 7/2009 | Sheffer | A61B 34/20 606/103 |
| 2010/0030223 | A1 | 2/2010 | Keller | |
| 2012/0078261 | A1 | 3/2012 | Kecman et al. | |
| 2012/0101505 | A1 | 4/2012 | Claypool et al. | |
| 2013/0030539 | A1 | 1/2013 | Wright et al. | |
| 2013/0079784 | A1 | 3/2013 | Vail et al. | |
| 2013/0184712 | A1 | 7/2013 | Choong et al. | |
| 2017/0281202 | A1* | 10/2017 | Hampp | A61B 34/20 |
| 2019/0209187 | A1 | 7/2019 | Hampp et al. | |
| 2021/0378683 | A1* | 12/2021 | Petteys | A61B 17/158 |
| 2023/0404598 | A1* | 12/2023 | Steeven | A61B 17/158 |
| 2024/0299042 | A1 | 9/2024 | Naybour et al. | |
| 2025/0009367 | A1* | 1/2025 | Petteys | A61B 34/10 |

* cited by examiner

PATELLA RESECTION GUIDE WITH INDEPENDENT ADJUSTMENT

CROSS-REFERENCE TO RELATED APPLICATIONS

The present application is a continuation of U.S. patent application Ser. No. 18/212,243, filed Jun. 21, 2023, which is a continuation of U.S. patent application Ser. No. 17/495,269, now U.S. Pat. No. 11,723,677, filed Oct. 6, 2021, which claims the benefit of the filing date of U.S. Provisional Pat. App. No. 63/092,675, filed Oct. 16, 2020, the disclosures of which are hereby incorporated herein by reference.

BACKGROUND

The patella is a sesamoid or lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging or disease, the articulating surfaces of the knee may degrade. To treat certain pathologies, it has become common to surgically remove the condyles and replace these structures with prosthetic implants. By the same processes, the articulating surfaces of the patella may also degrade. In connection with the implantation of a prosthetic knee, therefore, the articulating surface of the patella may also be replaced. Because of the tendons connected to the patella, it is generally advisable to replace only the articulating surfaces. An ultra-high-molecular-weight polyethylene articulating surface, with or without a metal baseplate or metal backing, is commonly implanted on the posterior side of the patella, adjacent the femoral condyles.

Typically, a surgeon selects a patellar prosthesis for implantation either by using a resurfacing technique wherein the prosthetic patella is resected and resurfaced and/or by an insetting procedure where the prosthetic patella is inserted into the prepared surface of the patella.

In either a total resurfacing procedure or a patella insetting procedure, it is important that a sufficient amount of bone stock remain after resection to accept the typical fixation pegs of the patellar prosthesis and maintain the integrity of the remaining patellar bone. Therefore, proper location of the saw blade is important. Known resection guides have saw guiding surfaces integrally formed or fixedly connected to clamping structures. Thus, the saw guiding surfaces, and by extension the resulting resection plane, may not be adjusted except by changing the placement of the clamping jaws on the patella. Reliable and secure placement of the jaws on the patella is hindered by the variability of patellar geometry, which frequently differs from the shape of patellar clamping jaws because such jaws are typically designed without respect to any specific patient's patella. Reliable and secure placement is made even more complicated by known resection guides in that the patella is tilted relative to the clamp in order to obtain the desired resection plane which creates awkward clamping angles and presents awkward bone geometries to the clamp.

BRIEF SUMMARY

According to an aspect of the disclosure, a patella resection guide may be provided with jaws for engagement to a patella, and an arm adjustable relative to the jaws. The arm may include a planar surface for guiding a cutting tool. The arm may be adjustable relative to the jaws and the frame of the guide in multiple directions. The frame may be the end blocks that retain the jaws and a bracket that connects the end blocks. The arm may be rotatable relative to the frame about two mutually transverse axes. The arm may also be translatable relative to the frame along another axis. The axes about or along which the arm may travel relative to the frame may be provided by mechanics of a linkage connecting the arm to the frame. The movement may be provided by mechanical interaction of features within the linkage. The movement may also be provided by mechanical interaction between features of the linkage and either or both of features of the frame and features of the arm.

One of the jaws of the guide may have a variable shape. The variability of the shape may be provided by movable mandibles within the jaw. The jaw may further include an immobile, fixed mandible between the two movable mandibles. The movable mandibles may be able to translate relative to the frame of the guide. The movable mandibles may be constrained to translation along mutually parallel tracks. The tracks may permit the movable mandibles to move toward or away from the opposite jaw.

According to another aspect, a patellar resection guide may include a frame, a first jaw, and a second jaw. The frame may include a first end and a second end opposed to the first end. The first jaw may be disposed at the first end of the frame. The second jaw may be disposed at the second end of the frame. The guide may further include an arm with a planar surface. The arm may be movably connected to the frame such that the arm is either or both of rotatable and translatable relative to the frame.

In some arrangements, the arm may be rotatable relative to the frame about two mutually transverse adjustment axes.

In some arrangements, the adjustment axes may be perpendicular to each other.

In some arrangements, the adjustment axes may be a first adjustment axis and a second adjustment axis. The arm may be connected to the frame such that rotation of the arm about the second adjustment axis changes the first adjustment axis.

In some arrangements, the first jaw and the second jaw may each include teeth extending along a frame plane. The second adjustment axis may extend parallel to the frame plane.

In some arrangements, the arm may be rotatable about the second adjustment axis to a position at which the first adjustment axis extends parallel to the frame plane.

In some arrangements, the planar surface of the arm may extend parallel to the first adjustment axis at all positions of the arm about the second adjustment axis.

In some arrangements, the arm may be connected to the frame by an adjustable linkage.

In some arrangements, the linkage may comprise a first link translatable relative to the frame along a first link translation axis.

In some arrangements, the guide may comprise a screw retained to the frame such that the screw is rotatable, but not translatable, about the first link translation axis. The first link may include an internally threaded bore threaded onto the first screw.

In some arrangements, the linkage may comprise a second link connected to the first link such that the second link may be rotatable relative to the first link about a second link rotation axis.

In some arrangements, the guide may comprise a screw. The second link may comprise a cylindrical barrel and an internally threaded eye through which a threaded portion of the screw is disposed. The first link may comprise a channel of arcuate axial cross section along which the barrel is disposed and a tab retained between flanges of the screw. The barrel and channel may both extend along the second link rotation axis.

In some arrangements, the guide may comprise a screw, a tab retained between two flanges of the screw and connected to the arm, and a cylindrical tube extending along an arm rotation axis and connected to the arm. The second link may include an internally threaded eye through which a threaded portion of the screw is disposed and a post extending within the tube along the arm rotation axis.

In some arrangements, the second jaw may be movably connected to the frame such that the second jaw is translatable toward or away from the first end of the frame.

In some arrangements, the first jaw may include two translatable mandibles each being independently translatable relative to the frame.

In some arrangements, the translatable mandibles may be translatable along respective parallel tracks.

In some arrangements, the guide may comprise a leaf spring biasing the translatable mandibles toward the second end of the frame.

In some arrangements, the first jaw may further include a fixed mandible disposed between the two translatable mandibles. The fixed mandible may be connected to the frame at a fixed position.

In some arrangements, each of the translatable mandibles may be translatable to a position relative to the frame at which at least one tooth of the respective translatable mandible extends further from the frame than the teeth of the fixed mandible.

In another aspect, a patellar resection guide may comprise a frame, an arm, a first jaw, and a second jaw. The frame may include a first end and a second end opposed to the first end. The arm may be connected to the frame and may have a guide surface. The first jaw may be disposed at the first end of the frame and may include two translatable mandibles that are each independently translatable relative to the frame. The second jaw may be disposed at the second end of the frame.

In some arrangements, the first jaw may include a fixed mandible disposed between the two translatable mandibles. The fixed mandible may be connected to the frame at a fixed position.

In some arrangements, the translatable mandibles may be biased to respective rest positions at which teeth extending from the translatable mandibles and fixed mandible are arrayed in an arc.

In some arrangements, the translatable mandibles may be translatable along respective parallel tracks.

In some arrangements, the guide may comprise a leaf spring biasing the translatable mandibles toward the second end of the frame.

In some arrangements, the guide surface may be a planar surface and the arm may be rotatably connected to the frame.

In some arrangements, the arm may be rotatable relative to the frame about two mutually transverse adjustment axes.

In some arrangements, the adjustment axes may be a first adjustment axis and a second adjustment axis, and rotation of the arm about the second adjustment axis changes the first adjustment axis.

In some arrangements, the first jaw and second jaw may each include teeth extending along a frame plane, and the arm is translatable relative to the frame along a third adjustment axis that extends normal to the frame plane.

In some arrangements, translation of the arm along the third adjustment axis relative to the frame may cause the first adjustment axis and second adjustment axis to translate relative to the frame.

In some arrangements, the second jaw may be movably connected to the frame such that the second jaw translates toward or away from the first end of the frame.

In another aspect, a method of treating a patella may comprise positioning a patellar resection guide relative to the patella. The guide may comprise a frame, a first jaw, a second jaw, and an arm. The guide may include a first end and a second end opposed to the first end. The first jaw may be disposed at the first end of the frame. The second jaw may be disposed at the second end of the frame. The arm may include a planar surface and may be movably connected to the frame such that the arm is rotatable relative to the frame. The method may comprise engaging the first jaw and the second jaw to the patella, rotating the arm relative to the frame until the planar surface is aligned with an intended patellar resection plane, and cutting the patella along the intended patellar resection plane by guiding a cutting tool along the planar surface.

In some arrangements, rotating the arm relative to the frame may include rotating the arm relative to the frame about two mutually transverse adjustment axes.

In some arrangements, engaging the first jaw to the patella may include causing two independently translatable mandibles included in the first jaw to conform to a contour of the patella.

In some arrangements, engaging the second jaw to the patella may include translating the second jaw relative to the frame toward the first end of the frame.

In another aspect, a method of resecting a patella to receive a prosthesis may include clamping a patella between first and second jaws of a guide assembly so that the patella is immoveable relative to the first and second jaws. The method may further include adjusting a guide arm having a guide surface relative to the first and second jaws and the patella clamped therebetween. The method may yet further include resecting the patella along a plane defined by the guide surface of the guide arm.

In some arrangements, the adjusting step may include rotating the guide surface about first and second axes.

In some arrangements, the first axis may be a medial-lateral axis and the second axis is a superior-inferior axis.

In some arrangements, the adjusting step may include translating the guide surface along a third axis.

In some arrangements, the method may include independently rotating first, second, and third adjustment members of the guide assembly so as to respectively adjust the guide surface about the first and second axes and along the third axis.

DETAILED DESCRIPTION

Figure 1:
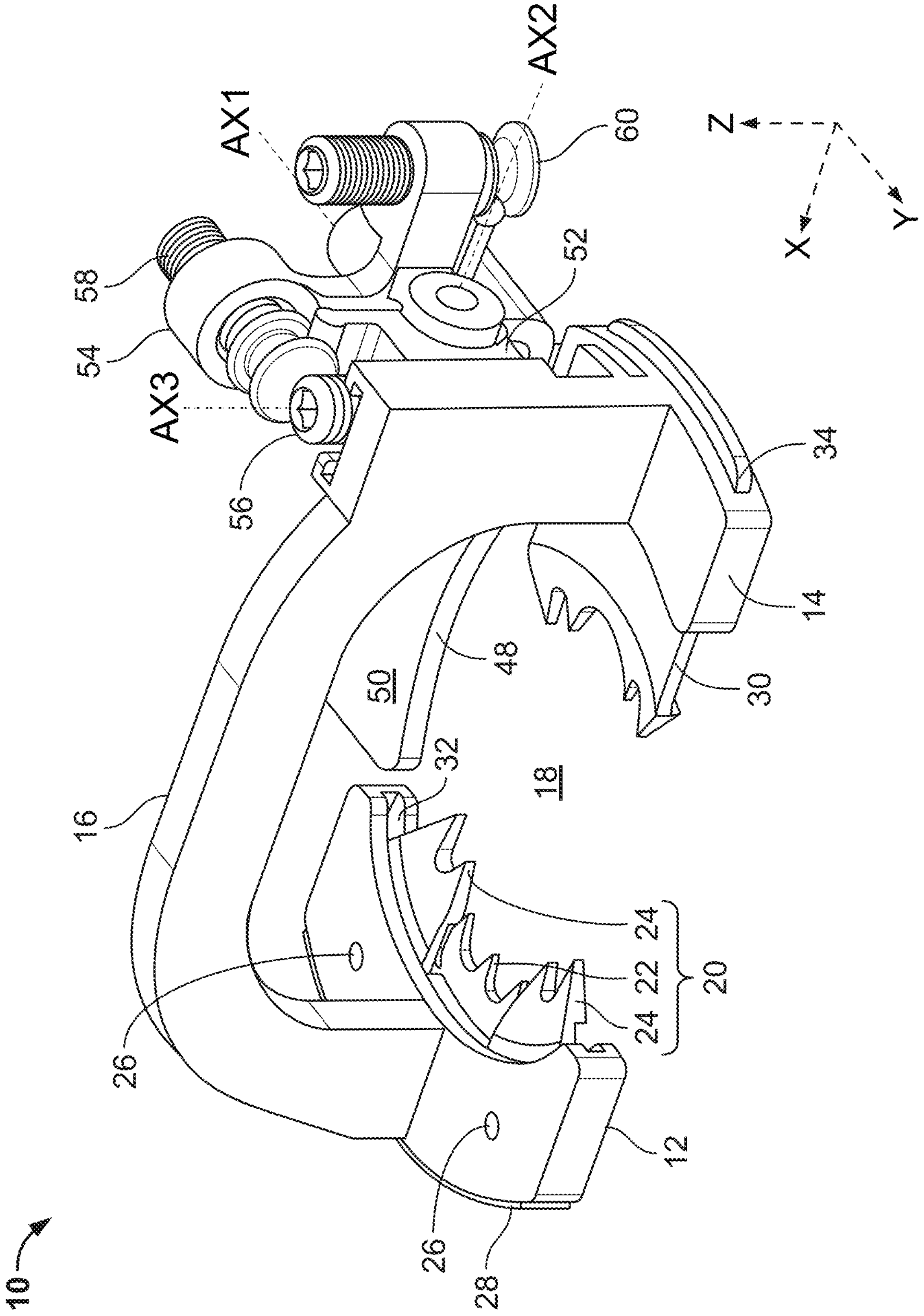
FIG. 1 is an oblique perspective view of a guide according to an aspect of the disclosure.

A patella resection guide 10 including a first end block 12 and a second end block 14 connected by a bracket 16, which collectively provide a frame of the guide 10, is illustrated in FIG. 1. The guide 10 is illustrated relative to a reference system including a height or vertical axis Z, a width or lateral axis Y, and a length or longitudinal axis X. Relative to this reference system, the first end block 12 provides a first end of the frame and the second end block 14 provides a second end of the frame opposed to the first end along the longitudinal axis X. The first end block 12 and second end block 14 both extend laterally in both directions, and curve slightly toward each other, away from their respective points of connection to the bracket 16. The first end block 12 and second end block 14 therefore define a generally elliptical receiving space 18 longitudinally between the first end block 12 and second end block 14, but aligned with the first end block 12 and second end block 14 on the vertical axis Z.

The bracket 16 defines a roughly arcuate shape on an X-Z plane, extending upward from and along the longitudinal axis X between the bracket's 16 respective points of attachment to the first end block 12 and the second end block 14. The bracket 16 therefore extends over the receiving space 18, and may be used as a handle for positioning the guide 10 to receive a patella in the receiving space 18.

Figure 2A:
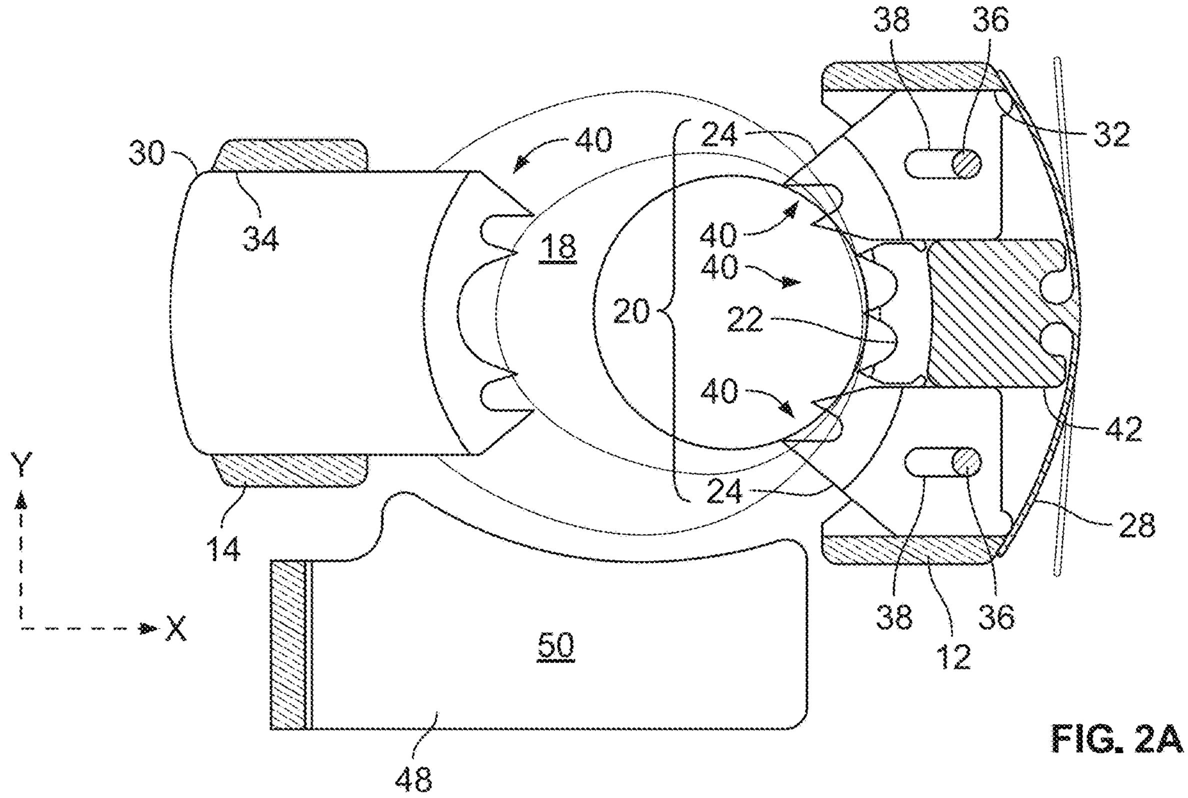
FIGS. 2A and 2B are views on a cross-section plane of the guide of FIG. 1 with a jaw conformed to different respective contours.
Figure 2B:
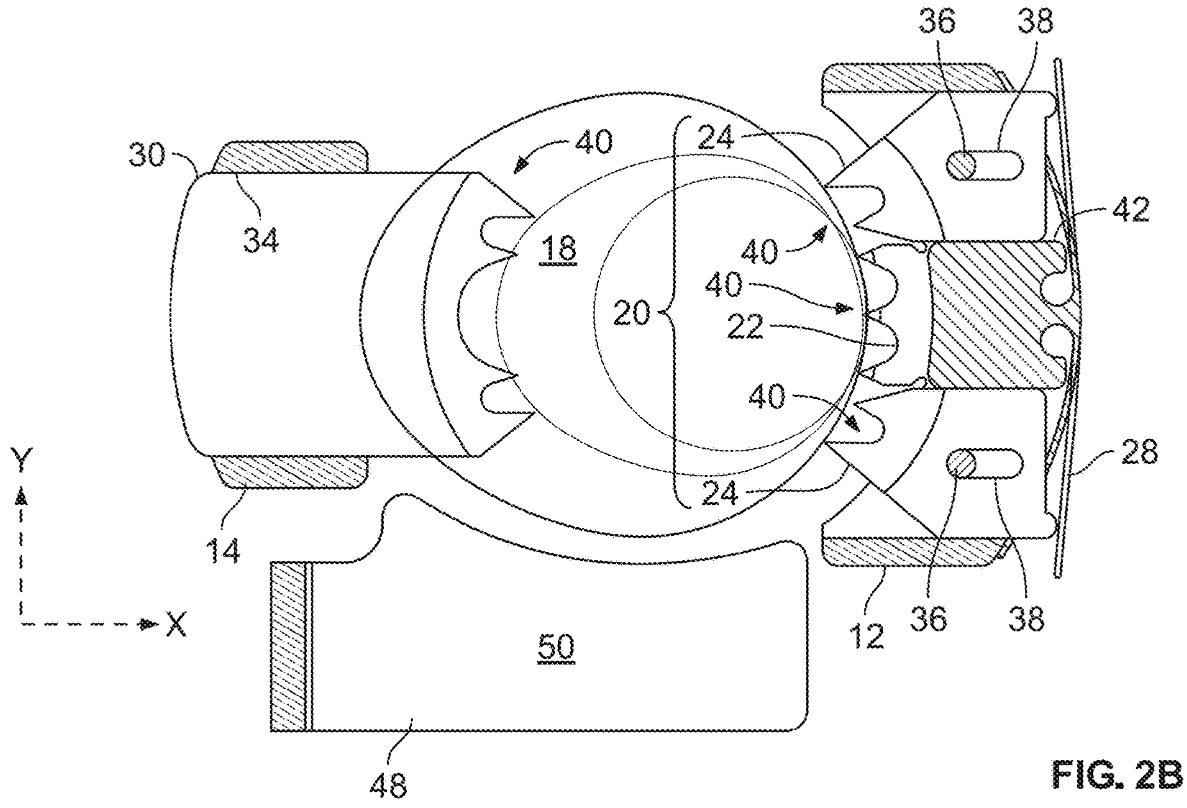
Figure 2C:
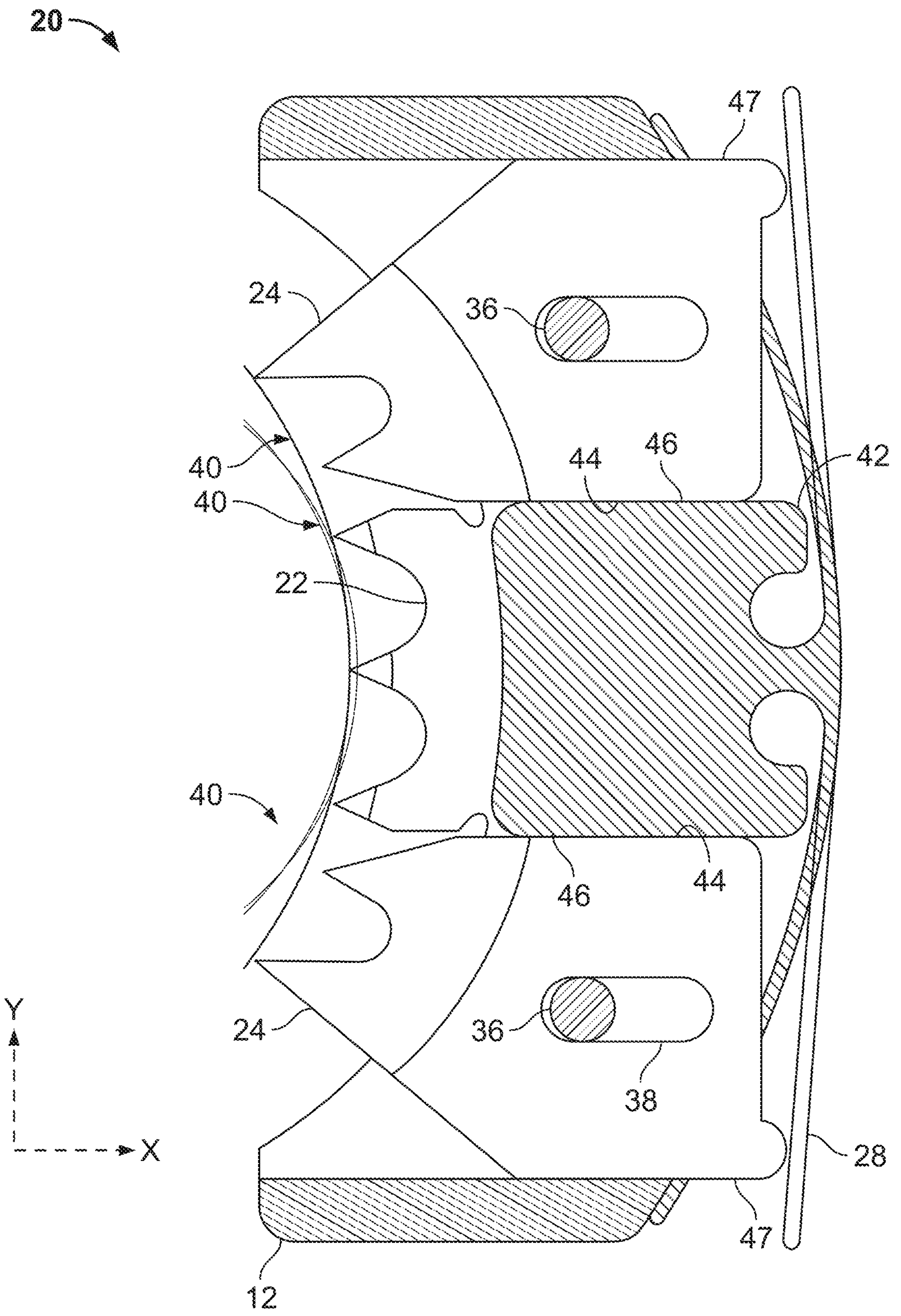
FIG. 2C is a close view on the cross-sectional plane of FIGS. 7A and 7B of a jaw of the guide of FIG. 1.

The first end block 12 encloses a first slot 32 and the second end block 14 encloses a second slot 34. The slots 32, 34 both extend on an X-Y plane. FIGS. 2A-2C are all cross-sectional views oriented downward along the vertical axis Z from a plane on which upper surfaces of both slots 32, 34 are defined.

Turning to FIGS. 2A-2C, with continued reference to FIG. 1, the first slot 32 houses elements of a first jaw 20, and the second slot 34 houses a second jaw 30. The first jaw 20 includes a fixed mandible 22 connected to the first end block 12, and thus the frame of the guide 10, at a fixed position centered within the slot of the first block 12 along the lateral axis Y under the bracket's 16 point of attachment to the first end block 12. In the illustrated example, the fixed mandible 22 is integrally formed with the first end block 12, and is provided by teeth 40 extending from a portion of the first end block 12 defining the lower edge of the first slot 32 into the receiving space 18. In other arrangements, the fixed mandible 22 is either or both of a discrete element and disposed within the first slot 32.

Also included in the first jaw 20 are two movable mandibles 24 disposed within the first slot 32 on either lateral side of the fixed mandible 22. The movable mandibles 24 are independently translatable within the first slot 32, and thus relative to the frame of the guide 10, along the longitudinal axis X. The first end block 12 includes two pinholes 26 for receiving pins 36 that extend into tracks 38 of the movable mandibles 24 to guide the translation of the movable mandibles 24.

With specific reference to FIG. 2C, the tracks 38 cooperate with the outer geometry of the movable mandibles 24 to constrain the movable mandibles 24 to translation parallel to the longitudinal axis X. Widths of the tracks 38 are closely fitted to diameters of the pins 36, which are fixed or fastened to the first end block 12. Further, a vertical thickness of the movable mandibles 24 is closely fitted to the height of the first slot 32. Motion of each movable mandible 24 relative to the first end block 12 is therefore constrained to translating on an X-Y plane in a direction aligned with the movable mandible's 24 respective track 38. A pillar 42 located in the lateral center of the first slot 32 extends from the upper edge of the first slot 32 to the lower edge of the first slot 32, and flat laterally inner edges 44 of the movable mandibles 24 slide along flat laterally outer edges 46 of the pillar 42. Because the respective abutting lateral edges 44, 46 of the movable mandibles 24 and the pillar 42 are both linear from the perspective of FIGS. 2A-2C, the movable mandibles 24 cannot rotate on the X-Y plane. The movable mandibles 24 are further prevented from rotating on the X-Y plane by similar engagement between laterally outer edges of the movable mandibles 24 and laterally inner edges of the first slot 32. The tracks 38 therefore cannot be rotated away from being mutually parallel and parallel to the longitudinal axis X. Thus, the movable mandibles 24, being constrained to translation in the direction of their respective tracks 38, are constrained relative to the frame of the guide 10 to translation parallel to the longitudinal axis X. In the illustrated arrangement, the movable mandibles 24 are therefore independently translatable, and their motion relative to the first end block 12 is limited to translation parallel to the longitudinal axis. In various other arrangements, the movable mandibles 24 are any one or any combination of conjoined, and thus not independently movable, able to rotate about axes parallel to the vertical axis Z, translatable along non-parallel tracks, and translatable along tracks 38 not parallel to the longitudinal axis X.

The movable mandibles 24 can translate to extend partially out of an opening of the first slot 32 opposite from the receiving space 18, as shown in FIGS. 2B and 2C. A leaf spring 28 is disposed on a side of the end block 12 opposite from the receiving space 18, attached to the pillar 42, and is biased toward a position at which the leaf spring 28 conforms to the side of the end block 12. Thus, the leaf spring 28 presses against the movable mandibles 24 if any portion thereof extends from the opening of the first slot 32 opposite from the receiving spaces 18. In the illustrated example, the leaf spring 28 specifically bears against round projections 47 at laterally outer corners of the movable mandibles 24, though in various arrangements the leaf spring 28 acts on any available surface of the movable mandibles 24. The leaf spring 28 thereby elastically biases the movable mandibles 24 longitudinally toward the second end block 14 and the second end of the frame of the guide 10. In other arrangements, biasing is achieved with biasing elements other than the leaf spring 28, or by one or more leaf springs attached in places other than that shown in FIGS. 2A-2C.

The movable mandibles 24 may be provided with a range of motion wherein the movable mandibles 24 extend from the opening of the first slot 32 opposite from the receiving space 18 at all positions within the range of motion, or at all positions except for the position closest to the second end block 14. Thus, each movable mandible 24 is biased by the leaf spring 28 toward a rest point, shown in FIG. 2A, which is the point within the movable mandible's 24 range of motion closest to the second end block 14, beyond which the leaf spring 28 cannot bias the movable mandible 24.

The mobility of the movable mandibles 24 enables the first jaw 20 to conform to a profile of a patella. Stability of the guide 10 relative to the patella generally improves as more teeth 40 sink into the patella, so the ability of the first jaw 20 to conform to the profile of the patella may improve the stability of the guide 10 while the patella is being cut. With both movable mandibles 24 in their respective rest position as illustrated in FIG. 2A, the teeth 40 of the first jaw 20 are arrayed in an arc on an X-Y plane, and are therefore prepared to engage an arcuate portion of a profile of a patella's surface. In the rest position of FIG. 2A, both teeth 40 of each of the movable mandibles 24 extend further into the receiving space 18 from the first end block 12 than the teeth 40 of the fixed mandible 22, and in the receded position of FIG. 2B, only one tooth 40 of each of the movable mandibles 24 extends further into the receiving space 18 from the first end block 12 than the teeth 40 of the fixed mandible 22. Thus, the teeth 40 of the first jaw are arrayed in a shallower arc in the receded position of FIG. 2B, and are therefore prepared to engage a flatter arcuate portion of a profile of a patella's surface than when in the position of FIG. 2A.

A second jaw 30 is translatably disposed within the second slot 34. The second jaw 30 can translate parallel to the longitudinal axis X within the second slot 34 of the second end block 14, and therefore relative to the frame of the guide 10, toward and away from the first end block 12 and the first end of the frame. The second jaw 30 can therefore translate partially out of the receiving space 18 to allow a patella to enter the receiving space 18, then back into the receiving space 18 to cooperate with the first jaw 20 to engage the patella. Translating actuation of the second jaw 30 may be accomplished with apparatuses not illustrated, such as a screw, ratchet, pinion gear, or any other mechanical devices capable of providing sufficient clamping force to give the teeth 40 sufficient purchase on the bone.

The teeth 40 all end in respective points on a common X-Y plane, termed a frame plane because it is the plane at which the frame of the guide 10 engages the bone. The teeth 40 of the fixed mandible 22 extend from the first end block 12 along the frame plane, while the teeth 40 of the movable mandibles 24 and the second jaw 30 slope downward from their respective origins on their respective mandible or jaw onto the frame plane. Thus, the teeth 40 of both jaws 20, 30 will engage a patella on a common plane. In other arrangements, the teeth 40 do not all align on a single plane. In such arrangements, the frame plane is defined as the plane on which the greatest number of points of the teeth 40 exist, and at least one of those points is associated with each of the first jaw 20 and the second jaw 30.

Returning to FIG. 1, the guide 10 further includes an arm 48, with an upper planar surface 50 along which a bone cutting tool is guided to resect the patella. The arm 48 is movably connected to the frame of the guide 10, and the bracket 16 specifically, by a linkage including a first link 52 and a second link 54. The first link 52 is connected to the bracket 16 by a first screw 56, a second screw 58 governs the position of the second link 54 relative to the first link 52, and a third screw 60 governs the position of the arm 48 relative to the second link 54. By turning the third screw 60, the arm 48 may be rotated relative to the bracket 16, first link 52, and second link 54 about a first adjustment axis AX1. By turning the third screw 58, the second link 54 and the arm 48 may be rotated relative to the bracket 16 and the first link 52 about a second adjustment axis AX2, which extends parallel to the longitudinal axis X. The second adjustment axis AX2 extends parallel to the lateral axis Y at one position of the second link 54 relative to the first link 52 and bracket 16, but turning the second screw 58 also changes the orientation of the first adjustment axis AX1. Turning the first screw 56 causes the first link 52, second link 54, and arm 48 to translate relative to the bracket 16 along a third adjustment axis AX3, which extends parallel to the vertical axis Z.

Figure 3A:
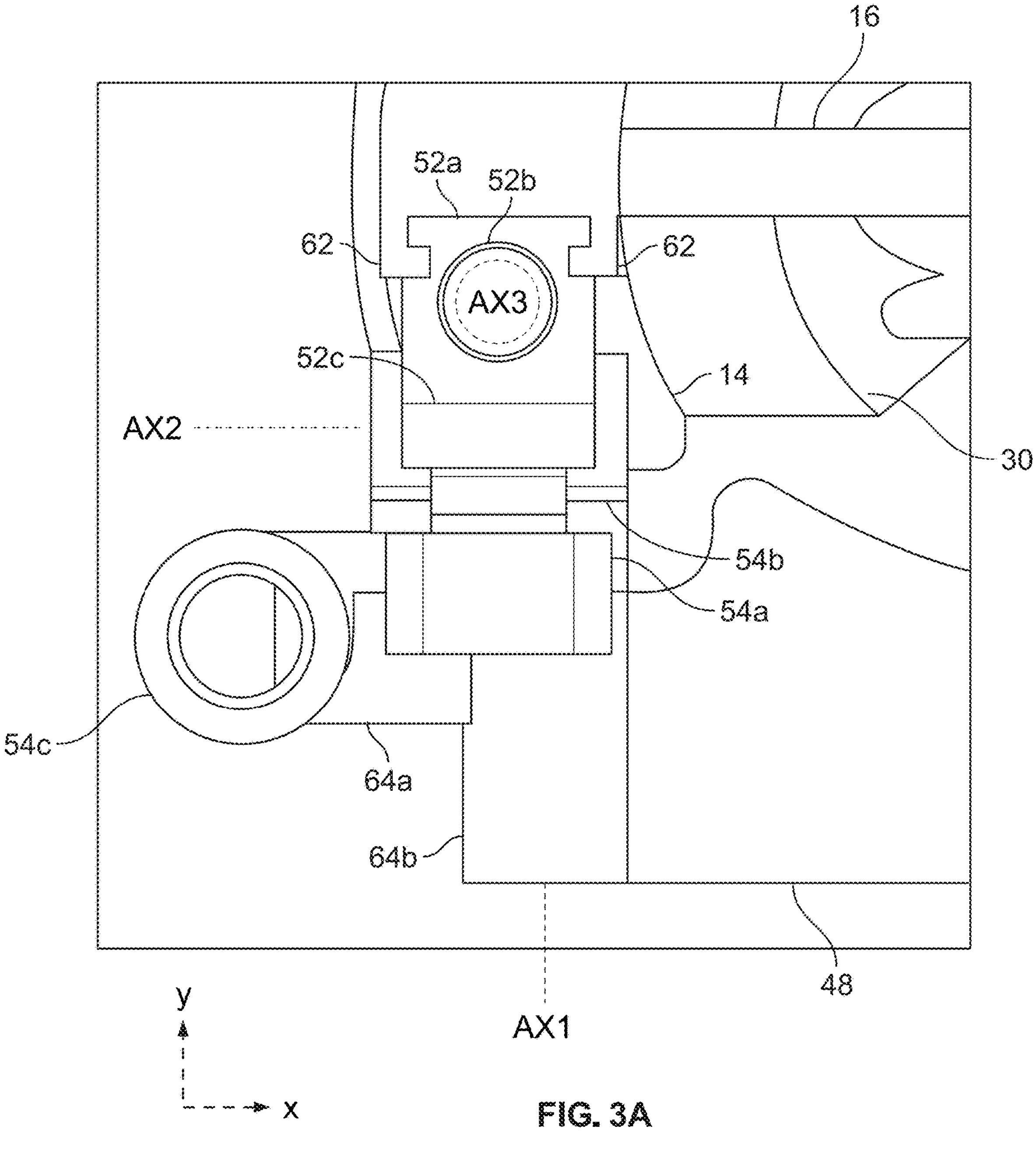
FIG. 3A is a top plan view of a portion of the guide of FIG. 1.
Figure 3B:
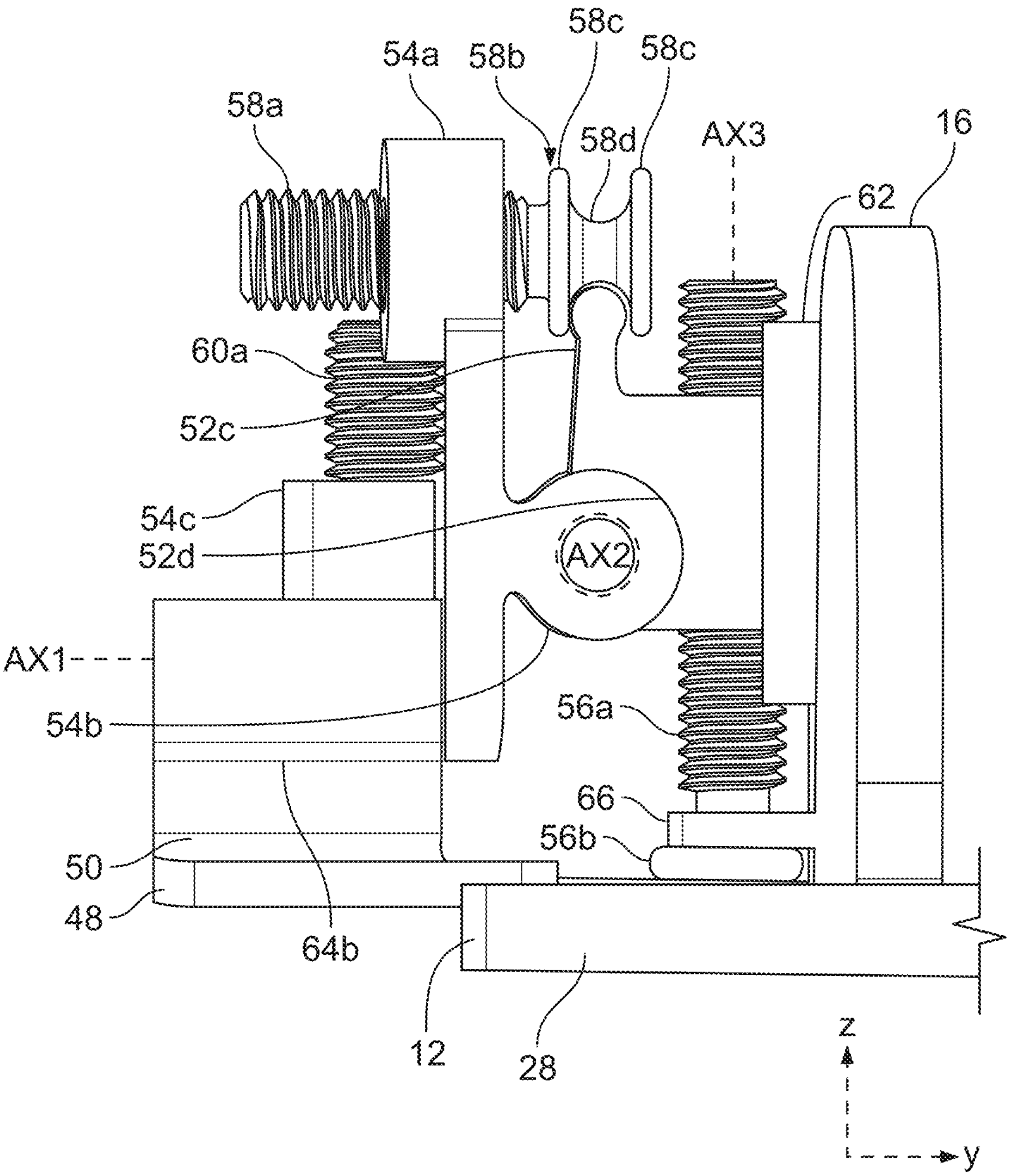
FIGS. 3B and 3C are side elevation views of the guide of FIG. 1.
Figure 3C:
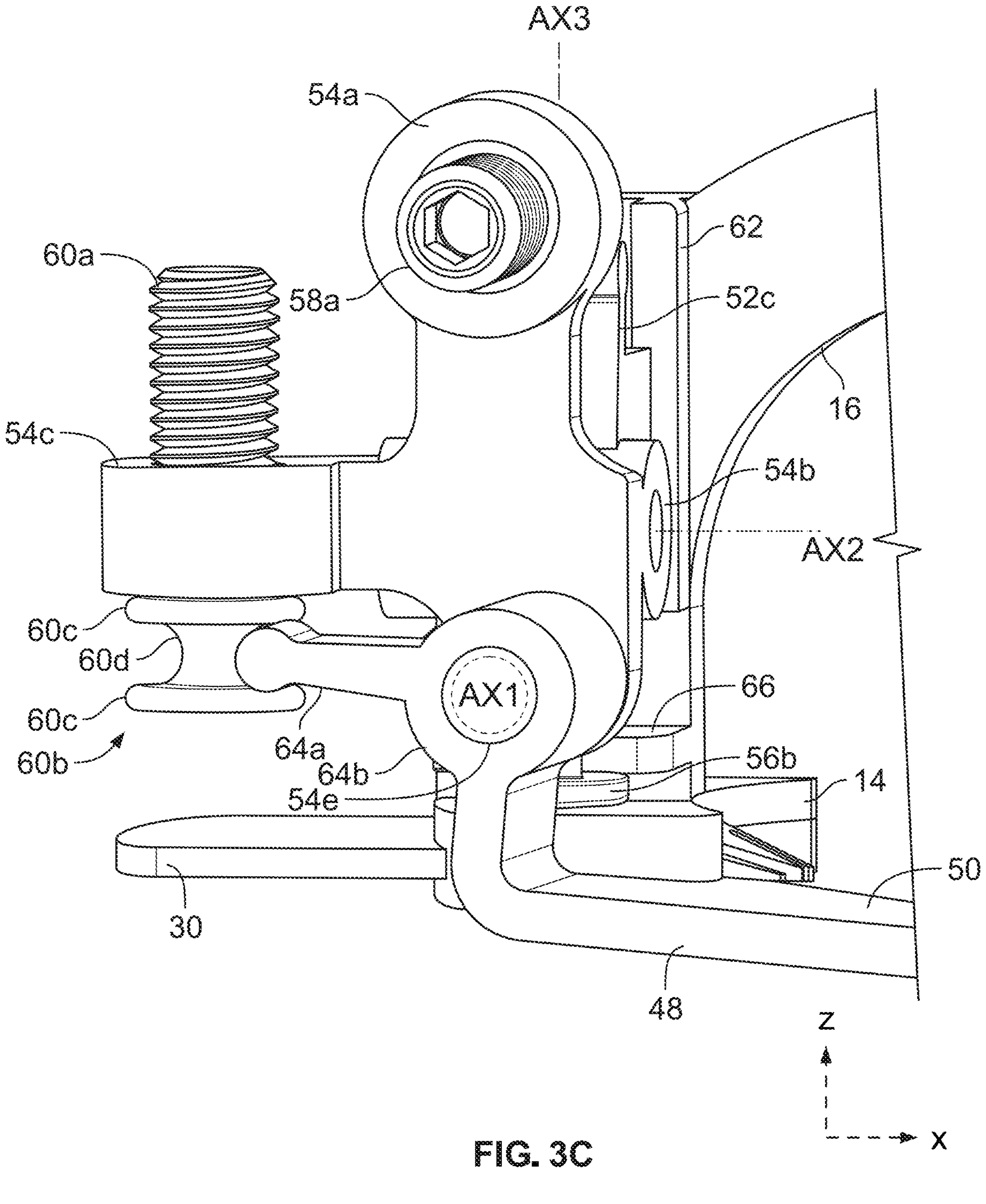

FIGS. 3A-3C illustrate the linkage in greater detail, with the screws 56, 58, 60 omitted from FIG. 3A. Referring specifically to FIG. 3A, opposed hooks 62 extend from a lateral face of the bracket 16 over the second end block 14. The hooks 62 mirror each other to form a vertical track along which a flange 52*a* of the first link 52 slides. The first link 52 also includes an internally threaded bore 52*b* extending through the first link 52 parallel to the vertical track provided by the hooks 62. The threaded shank 56*a* of the first screw 56 extends through the bore 52*b*, as shown in FIG. 3B. The first screw 56 ends at a flat first screw head 56*b* bearing against an upper surface of the second end block 14. A narrowed portion of the first screw 56 between the threaded shank 56*a* and the head 56*b* is retained by a collar 66 extending from the same side of the bracket 16 as the opposed hooks 62. The head 56*b* is trapped between the collar 66 and the upper surface of the second end block 14, so the first screw 56 is unable to translate relative to the bracket 16. Turning the first screw 56 within the internally threaded bore 52*b* therefore causes the first link 52 to translate vertically relative to the bracket 16, with the flange 52*a* sliding along the vertical track provided by the two opposed hooks 62. The second link 54 and the arm 48 are both connected to the bracket 16 through the first link 52, so translation of the first link 52 relative to the bracket 16 causes the second linked 54 and the arm 48 to translate relative to the bracket 16 as well.

With continued reference to FIGS. 3A and 3B in particular, the second screw 58 governs rotation of the second link 54 relative to the first link 52. The first link 52 includes a vertical tab 52*c* that cooperates with a spool 58*b* at an end of the second screw 58. The spool 58*b* is provided by two discs 58*c* defining opposite sides of an annular groove 58*d*. The vertical tab 52*c* extends between the two discs 58*c* into the annular groove 58*d*, and is abutted on either side by the discs 58*c*. A threaded shank 58*a* of the second screw 58 extends from the spool 58*b* through an internally threaded first eye 54*a* of the second link 54. Because the discs 58*c* of the spool 58*b* abut either side of the vertical tab 52*c*, rotation of the threaded shank 58*a* of the second screw 58 within the internally threaded first eye 54*a* causes the first eye 54*a* to travel toward or away from the vertical tab 52*c*.

The second link 54 includes a cylindrical barrel 54*b*, a centerline of which defines the second adjustment axis AX2, and the barrel 54*b* is aligned within a channel 52*d* in the first link 52 that has an arcuate cross-sectional profile on planes perpendicular to the second adjustment axis AX2. The placement of the barrel 54*b* within the channel 52*d* and the extension of the vertical tab 52*c* into the spool 58*b* cooperate to limit travel of the second link 54 relative to the first link 52 to rotation about the second adjustment axis AX2. Thus, travel of the internally threaded first eye 54*a* toward or away from the vertical tab 52*c* caused by rotation of the threaded shank 58*a* of the second screw 58 within the first eye 54*a* corresponds to pivoting of the second link 54 relative to the first link 52 about the second adjustment axis AX2. Further, translation of the first link 52 along the third adjustment axis AX3 causes corresponding translation of the second adjustment axis AX2 as the barrel 54*b* travels along with the first link 52 and second link 54.

Turning to FIG. 3C, with continued reference to FIG. 3B, the arm 48 is rotatably connected to the second link 54 by a tube 64*b* integrally formed with the arm and a post 54*c* of the second link 54 that extends through the tube 64*b*. Because the tube 64*b* may rotate about the post 54*c*, the first adjustment axis AX1 is defined along a centerline of a cylindrical shape of the post 54*c*. The first adjustment axis AX1 therefore rotates about the second adjustment axis AX2 whenever the second link 54 rotates about the second adjustment axis AX2, and the first adjustment axis AX1 translates vertically whenever the first link 52 and second link 54 translate along the third adjustment axis AX3. At one position of the second link 54 about the second adjustment axis AX2, the post 54*e* and first adjustment axis AX1 extend parallel to the lateral axis Y.

The third screw 60 governs rotation of the arm 48 relative to the second link 54. The third screw 60 includes a threaded shank 60*a* extending through an internally threaded second eye 54*c* of the second link 54, and ends in a spool 60*b* that interacts with a rotatable tab 64*a* integrally connected to the tube 64*b* and the arm 48. The spool 60*b* of the third screw 60 includes two discs 60*c* defining opposite sides of an annular groove 60*d*. The rotatable tab 64*a* extends between the two discs 60*c* into the annular groove 60*d*, where it is abutted on either side by the discs 60*c*. Thus, rotation of the threaded shank 60*a* of the third screw 60 within the second eye 54*c* will cause a free end of the rotatable tab 64*a* to travel toward or away from the second eye 54*c*. Because the arm 48 and rotatable tab 64*a* are connected to the second link 54 by a close fit of the tube 64*b* around the post 54*c*, travel of the free end of the rotatable tab 64*a* toward or away from the second eye 54*c* corresponds to rotation of the rotatable tab 64*a*, tube 64*b*, and arm 48 about the first adjustment axis AX1.

After the guide 10 is fixed to the patella with the jaws 20, 30, the surgeon may use a driver 68 to orient the arm 48 to align the planar surface 50 with an intended resection plane as shown in FIGS. 4A-6B. In the illustrated example, the first screw 56*a* includes a hexagonal recess at an end of the threaded shank 56*a* opposite from the head 56*b*. Similarly, the second screw 58 includes a hexagonal recess at an end of the threaded shank 58*a* opposite from the spool 58*b* of the second screw 58, and the third screw 60 includes a hexagonal recess at an end of the threaded shank 60*a* opposite from the spool 60*b* of the third screw 60. Accordingly, the driver 68 of the illustrated example therefore ends in a projection for rotationally engaging the hexagonal recesses in the screws 56, 58, 60. However, in various other examples, the driver 68 is any other driving feature, such as a square head, flat head, Phillips head, or a shaped recess, and the screws 56, 58, 60 include whatever features other than a hexagonal recess that match the driver 68.

Figure 4A:
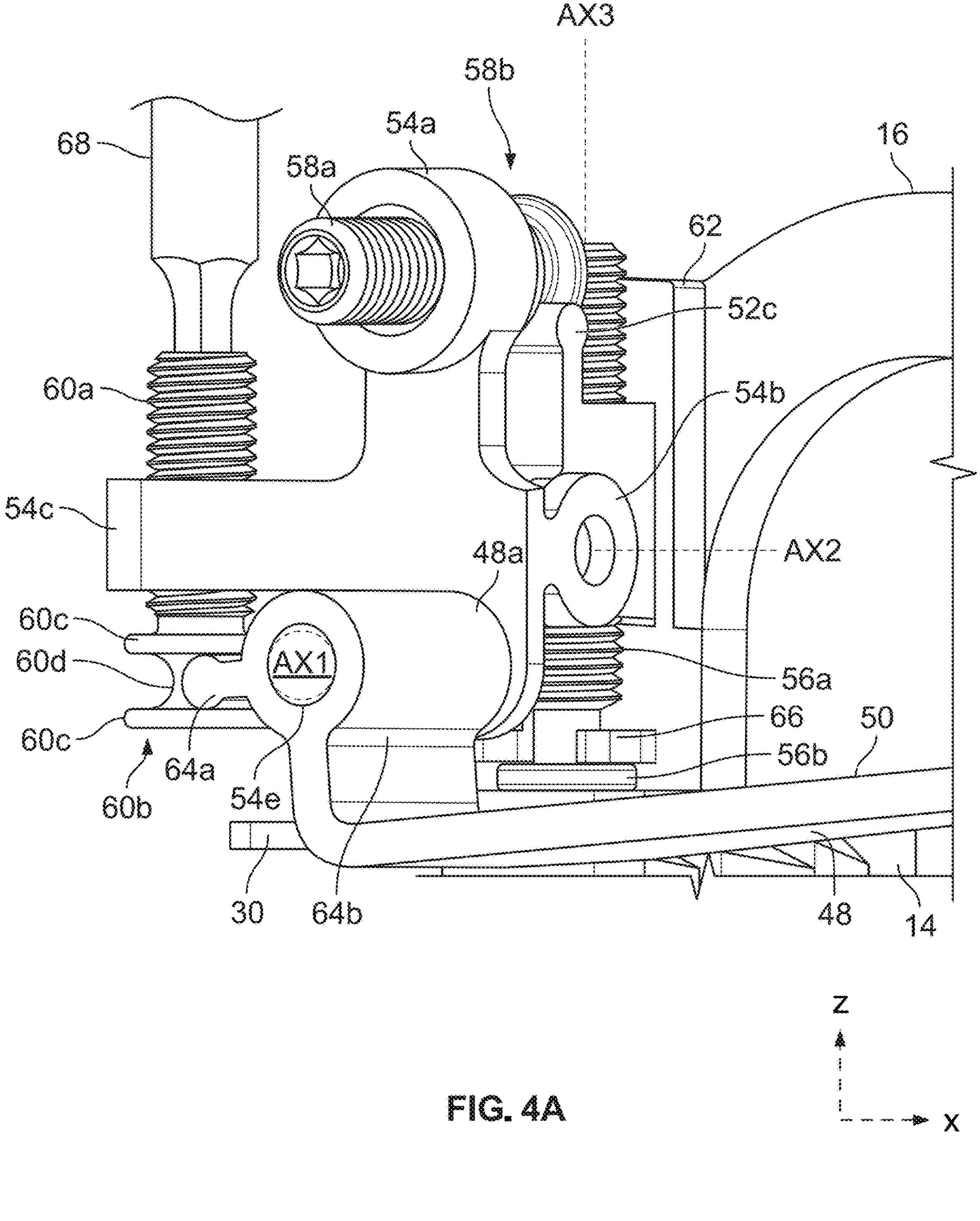
FIGS. 4A and 4B are side elevation views of the guide of FIG. 1 adjusted to different respective positions about an axis.
Figure 4B:
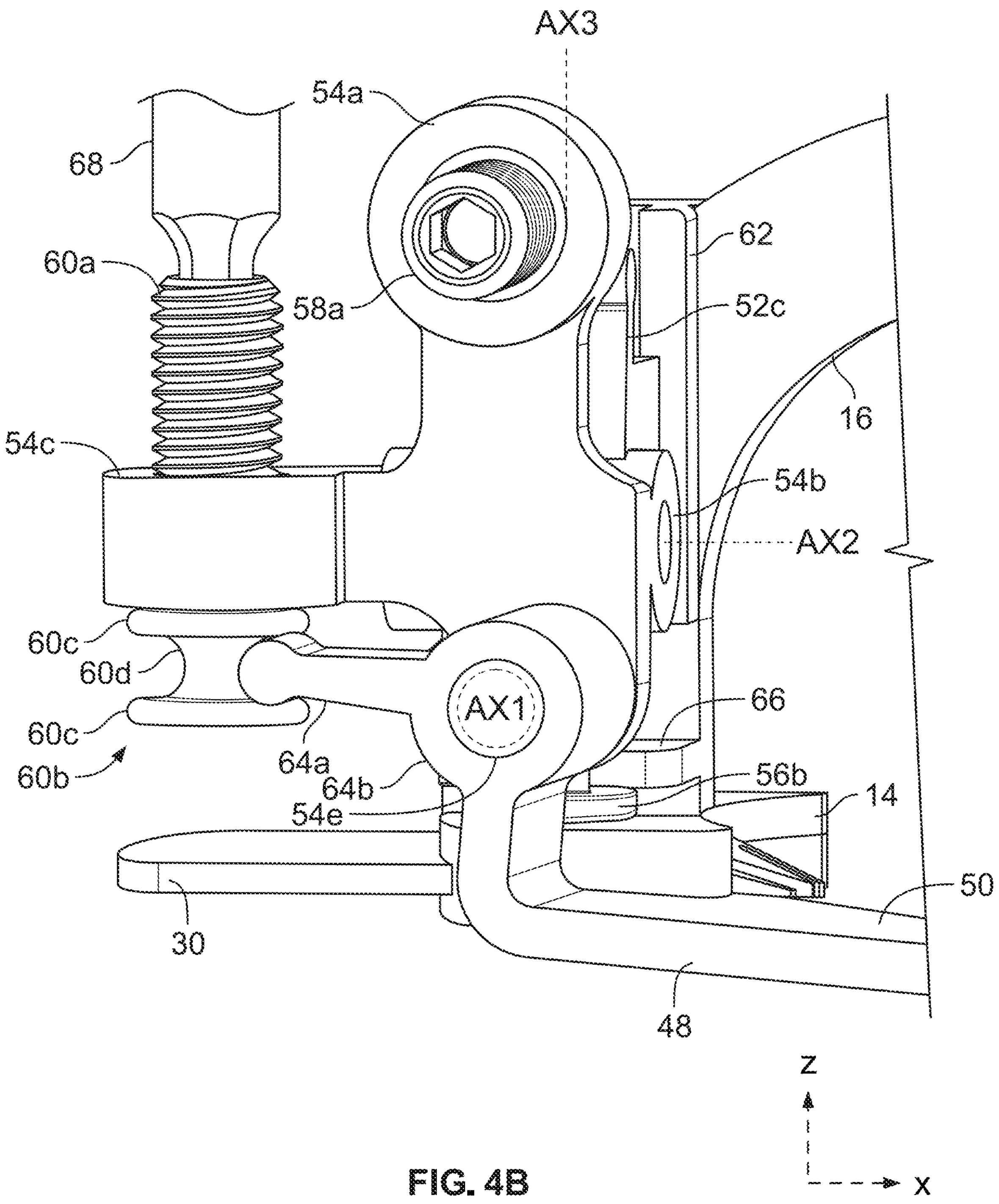
Figure 5A:
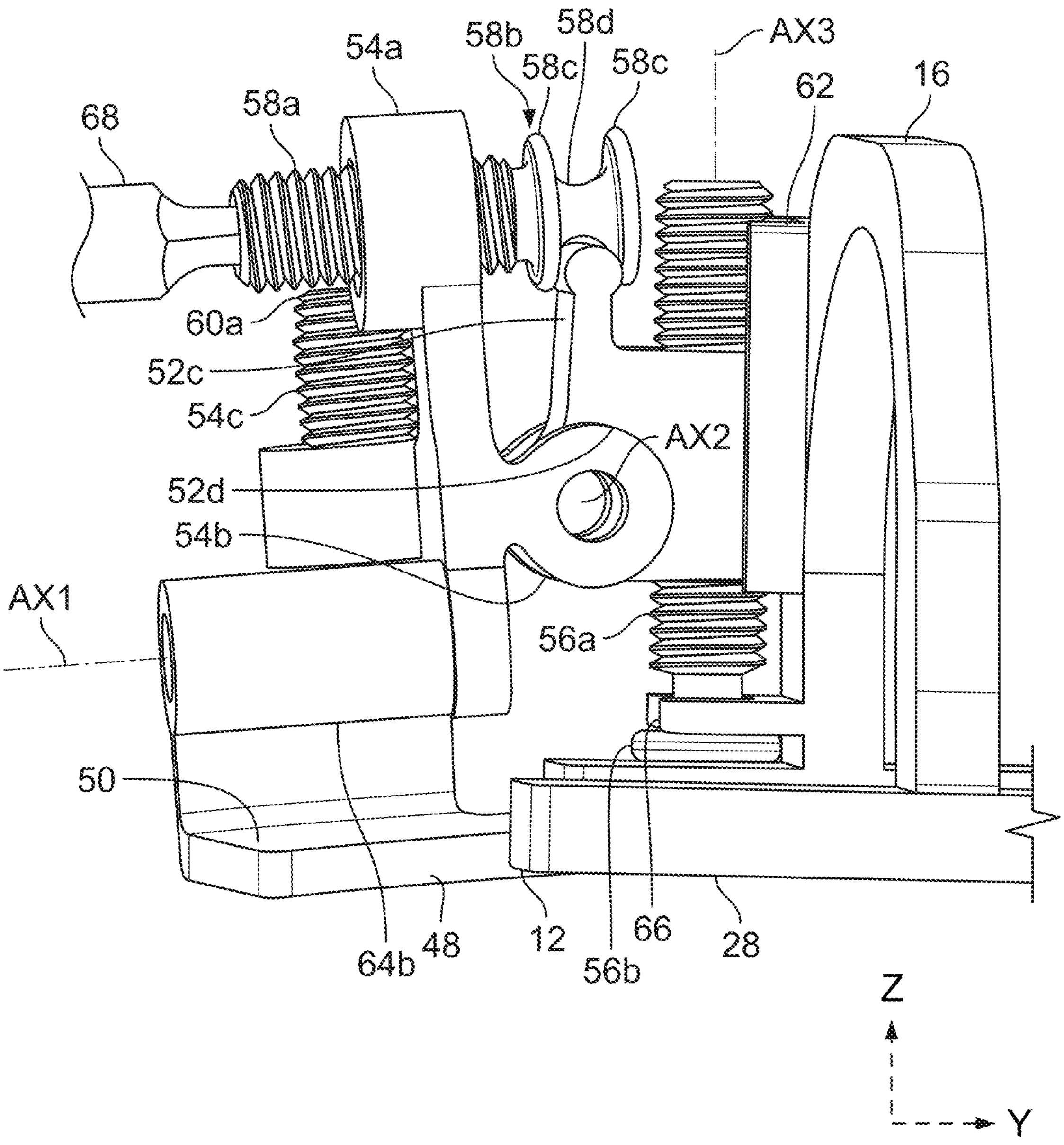
FIGS. 5A and 5B are side elevation views of the guide of FIG. 1 adjusted to different respective positions about another axis.
Figure 5B:
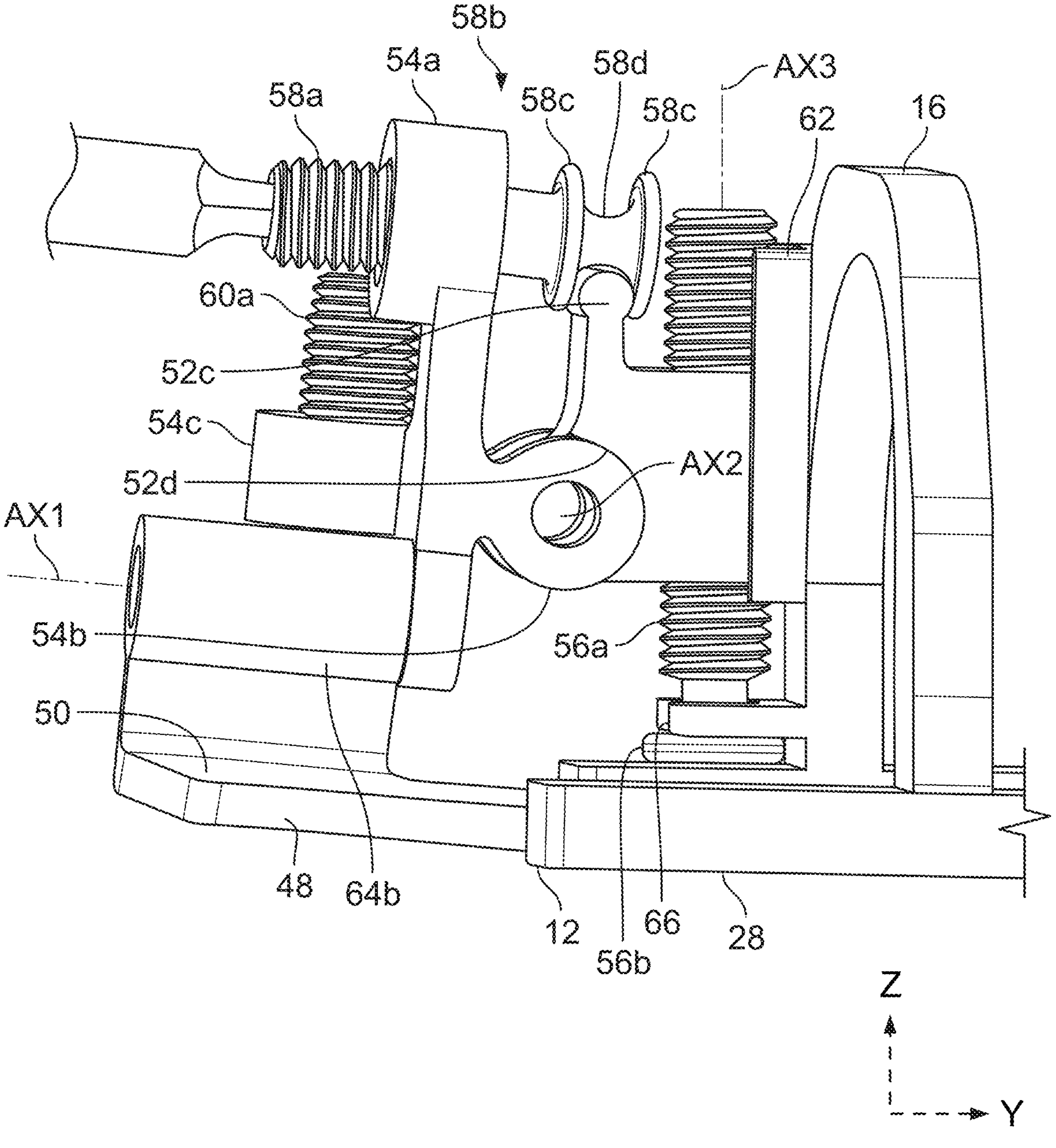
Figure 6A:
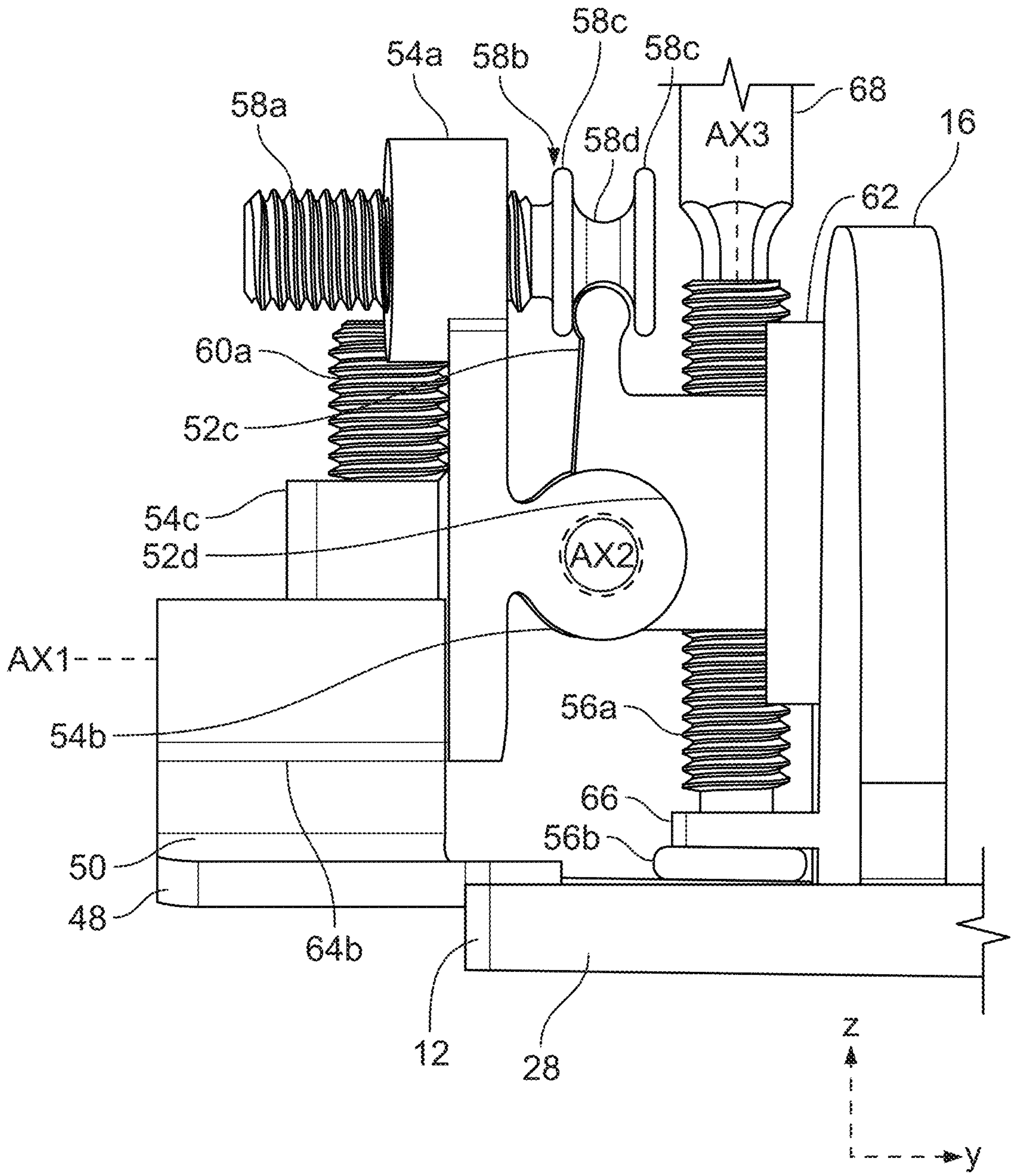
FIGS. 6A and 6B are side elevation views of the guide of FIG. 1 adjusted to different respective positions about yet another axis.
Figure 6B:
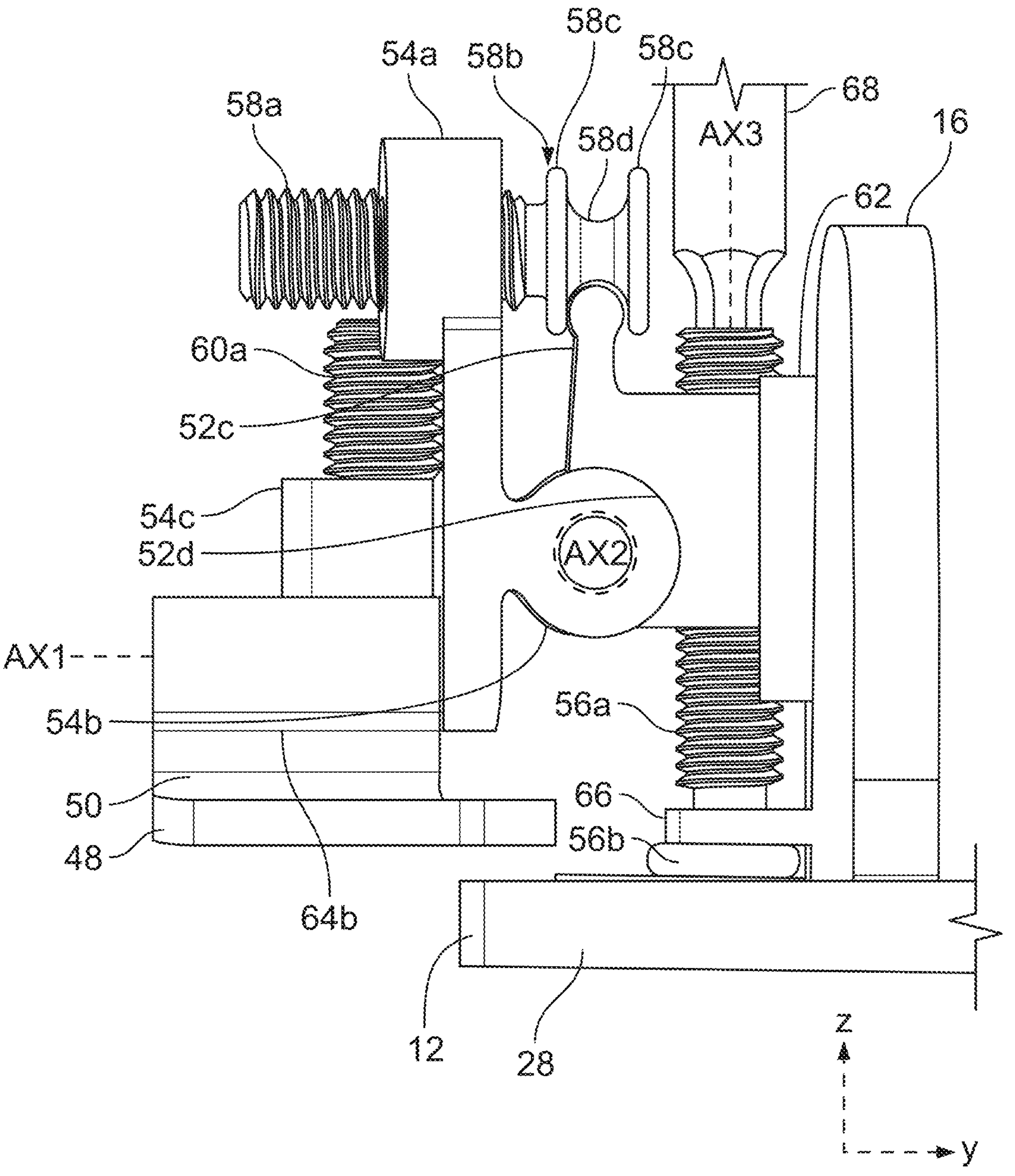

The surgeon may begin a process of positioning the arm 48 by engaging the driver 68 to the third screw 60, and using the driver 68 to turn the third screw 60 to rotate the arm 48 about the first adjustment axis AX1. First adjustment axis AX1 is generally parallel to a superior-inferior axis of the patella such that turning the third screw 60, as shown in FIGS. 4A and 4B, causes arm 50 to rotate about first adjustment axis AX1 thereby adjusting the lateral-medial tilt of the resection plane. Next, the surgeon may engage the driver 68 to the second screw 58 and use the driver 68 to rotate the arm 48 about the second axis AX2. Second adjustment axis AX2 is generally parallel to the lateral-medial axis of the patella such that turning the second screw 58, as shown in FIGS. 5A and 5B, causes arm 50 to rotate about second adjustment axis AX2 thereby adjusting the superior-inferior tilt of the resection plane. As used here, the terms superior, inferior, medial, and lateral refer to anatomical directions relative to the body of the patient in one contemplated orientation of the guide 10 on a patella, but these terms are not limiting. That is, the guide 10 may be oriented otherwise on the patella, and other arrangements of the guide 10 may include various features at different positions relative to the patient. For example, the linkage may be connected to the bracket 16 at other positions, such as on an opposite side of the bracket 16 from what is illustrated, or over the first end block 12 instead of the second end block 14. Finally, the surgeon may engage the driver 68 to the first screw 56 and use the driver 68 to translate the arm 48 along the third adjustment axis AX3 downward or upward (i.e., anterior and posterior) as shown in FIGS. 6A and 6B, respectively. Translating the arm 48 along the third adjustment axis AX3 adjusts the depth of the resection and the respective thicknesses of the removed and remaining portions of the patella.

Though the process described above lists adjusting the arm 48 relative to the first adjustment axis AX1, then the second adjustment axis AX2, then the third adjustment axis AX3, the surgeon may adjust the arm 48 relative to the adjustment axes AX1, AX2, AX3, in any order. Positioning the arm 48 may involve iterative adjustment about each of the adjustment axes AX1, AX2, AX3, such as returning to a previously adjusted axis once or more after moving the arm 48 relative to either or both of the other two axes.

Figure 7A:
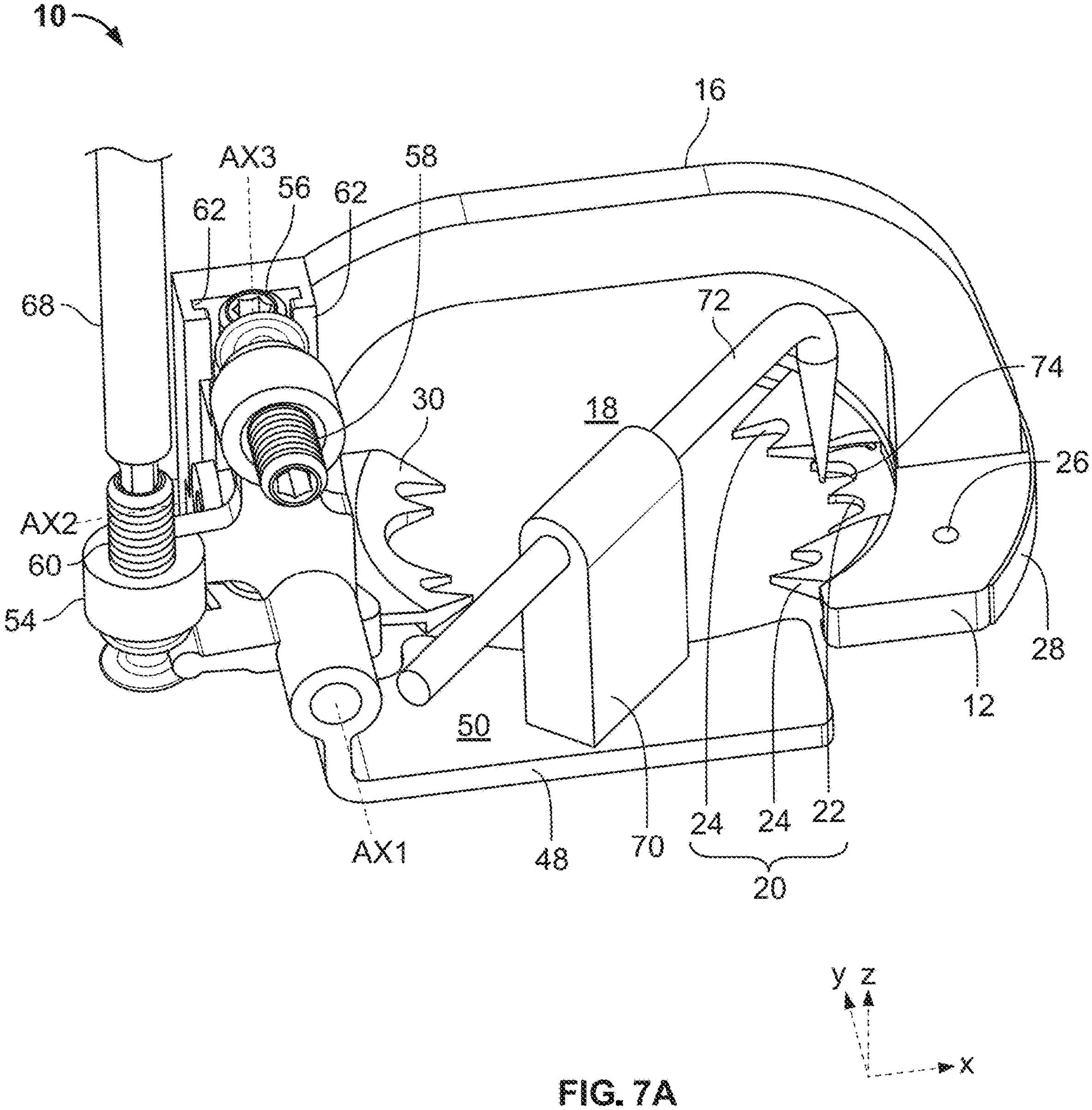
FIGS. 7A and 7B are perspective views of the guide of FIG. 1 in use with a stylus.
Figure 7B:
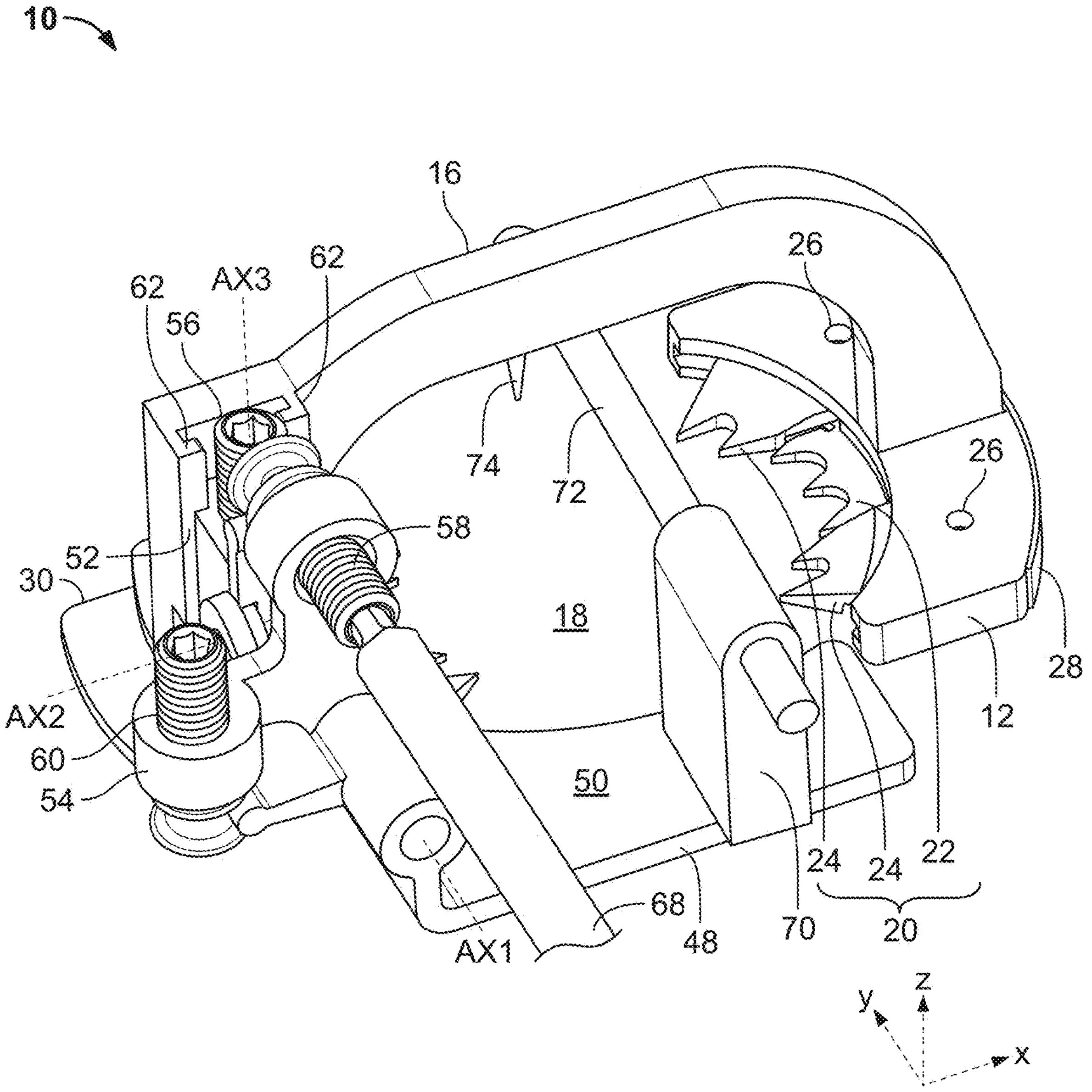

A positioning block 70 and stylus 72 may be used to aid the positioning process of the arm 48 described above as illustrated in FIGS. 7A and 7B. The stylus 72 is slidably retained by the positioning block 70. The stylus 72 and positioning block 70 are respectively dimensioned such that the tip 74 of the stylus 72 will exist on the plane of the planar surface 50 of the arm 48 when the positioning block 70 is placed on the planar surface 50 and both the tip 74 and the positioning block 70 are oriented to extend normal to the planar surface 50 as shown in FIGS. 7A and 7B. Thus, the tip 74 of the stylus 72 may be used to indicate where the resection plane corresponding to a given position of the arm 48 will intersect an object, such as the patella. The above described process of positioning the arm 48 may therefore include probing superior and inferior poles of the patella with the stylus 72 as shown in FIG. 7A, and probing medial and lateral edges of the patella 72 as shown in FIG. 7B. Arm 50 is adjusted as described above to ensure stylus contact at the desired positions so as to confirm and gauge the resection plane.

Figure 8:
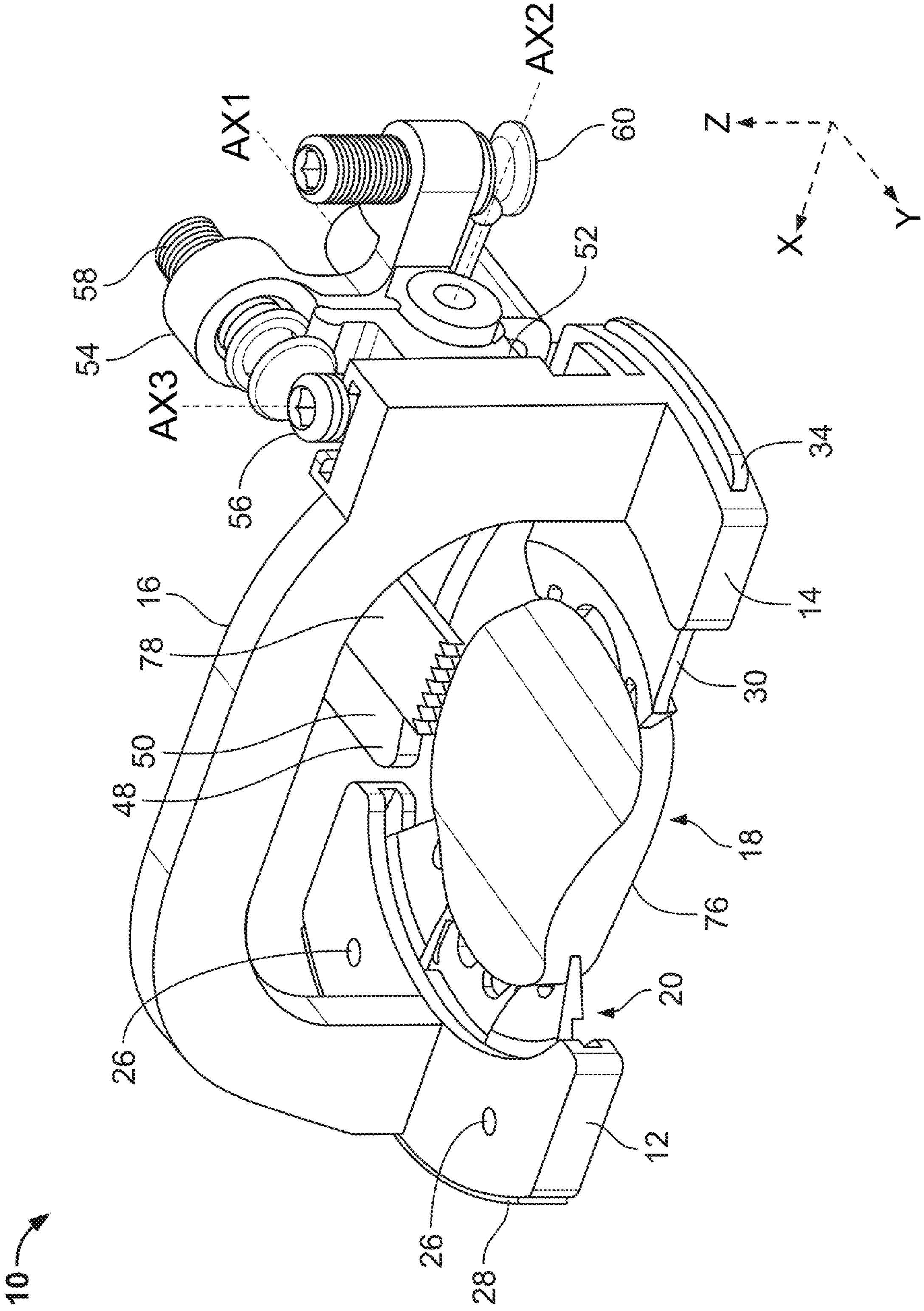
FIG. 8 is an oblique perspective view of the guide of FIG. 1 in use with a patella and cutting tool.
Figure 9:
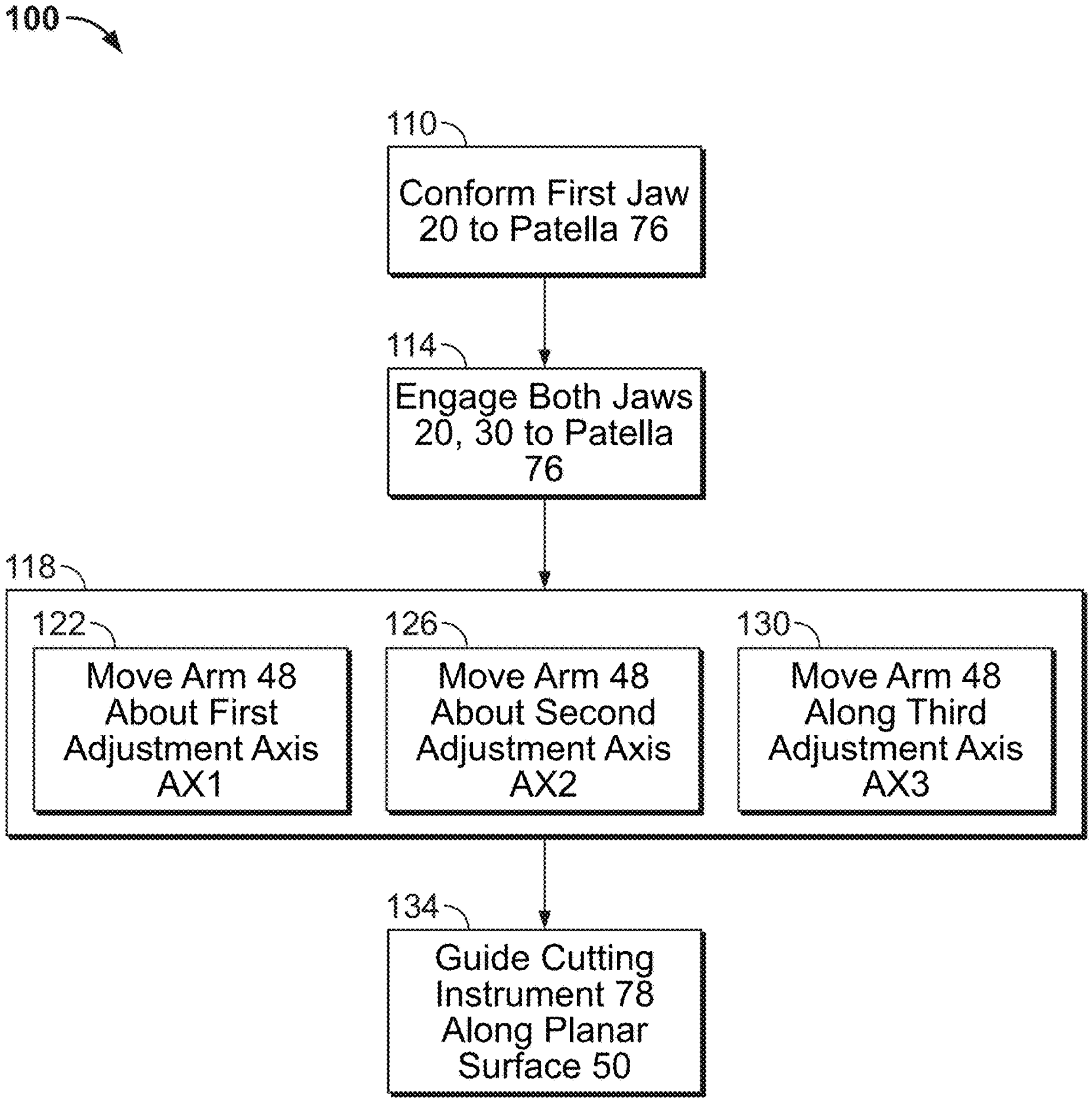
FIG. 9 is a flowchart illustrating a process for using the guide of FIG. 1.

Finally, with the jaws 20, 30 engaged to a patella 76, a cutting tool 78 may be guided along the planar surface 50 of the arm 48 as shown in FIG. 8. A summary of a process 100 for using the guide 10 generally as described above is provided in FIG. 9. At block 110, the surgeon conforms the first jaw 20 to the patella 76. In the illustrated example, the first jaw 20 is conformed to a superior or inferior pole of the patella 76. Conforming the first jaw 20 to the patella 76 includes allowing or causing the movable mandibles 24 to translate relative to the first end block 12 to a position where the teeth 40 of the movable mandibles 24 and fixed mandible 22 are arrayed to generally match the profile of the portion of the patella 76 that the first jaw 20 is intended to engage.

In some examples, block 110 is omitted, and in others, block 110 occurs as part of block 114.

At block 114, the first jaw 20 and second jaw 30 are engaged to the patella 76 by causing the teeth 40 of both jaws to sink into the patella 76. The engagement may include applying force to the second jaw 30 along the longitudinal axis X toward the first jaw 20 while applying an opposing force to the frame of the guide 10. Engaging the first jaw 20 may also include applying force directly to the movable mandibles 24 along the longitudinal axis X toward the second jaw 30.

At stage 118, the arm 48 is positioned relative to the patella 76 to align the planar surface 50 with the intended resection plane. Adjusting the position of the arm 48 includes using the driver 68 to adjust the arm 48 about the first adjustment axis AX1 at block 122, about the second adjustment axis AX2 at block 126, and along the third adjustment axis AX3 at block 130. At state 118, the surgeon may adjust the arm 48 about the first adjustment axis AX1 first, then the second adjustment axis AX2 second, followed by finally adjusting the arm along the third adjustment axis AX3. The surgeon may also adjust the arm 48 relative to the adjustment axes AX1, AX2, and AX3 in any other order, and may readjust relative to any of the adjustment axes AX1, AX2, AX3 as many times as necessary to place the arm 48 at an acceptable orientation. With the arm 48 so placed, the surgeon guides the cutting instrument 78 along the planar surface 50 to cut the patella 76 at block 134.

The features of the above described guide 10 may be varied, rearranged, or combined with features of other guides. For example, the first jaw 20 having movable mandibles 24 in cooperation with a fixed mandible 22 may be implemented in place of any stationary jaw in other patella resection guides. In another example, other patella resection guides may be provided with an arm having a planar surface for guiding a cutting tool movable in any one or any combination of the ways described above. Moreover, in other arrangements of the guide 10 of the present disclosure, individual features associated with either of the first end block 12 and the second end block 14 may be transferred to the other end block.

Figure 10A:
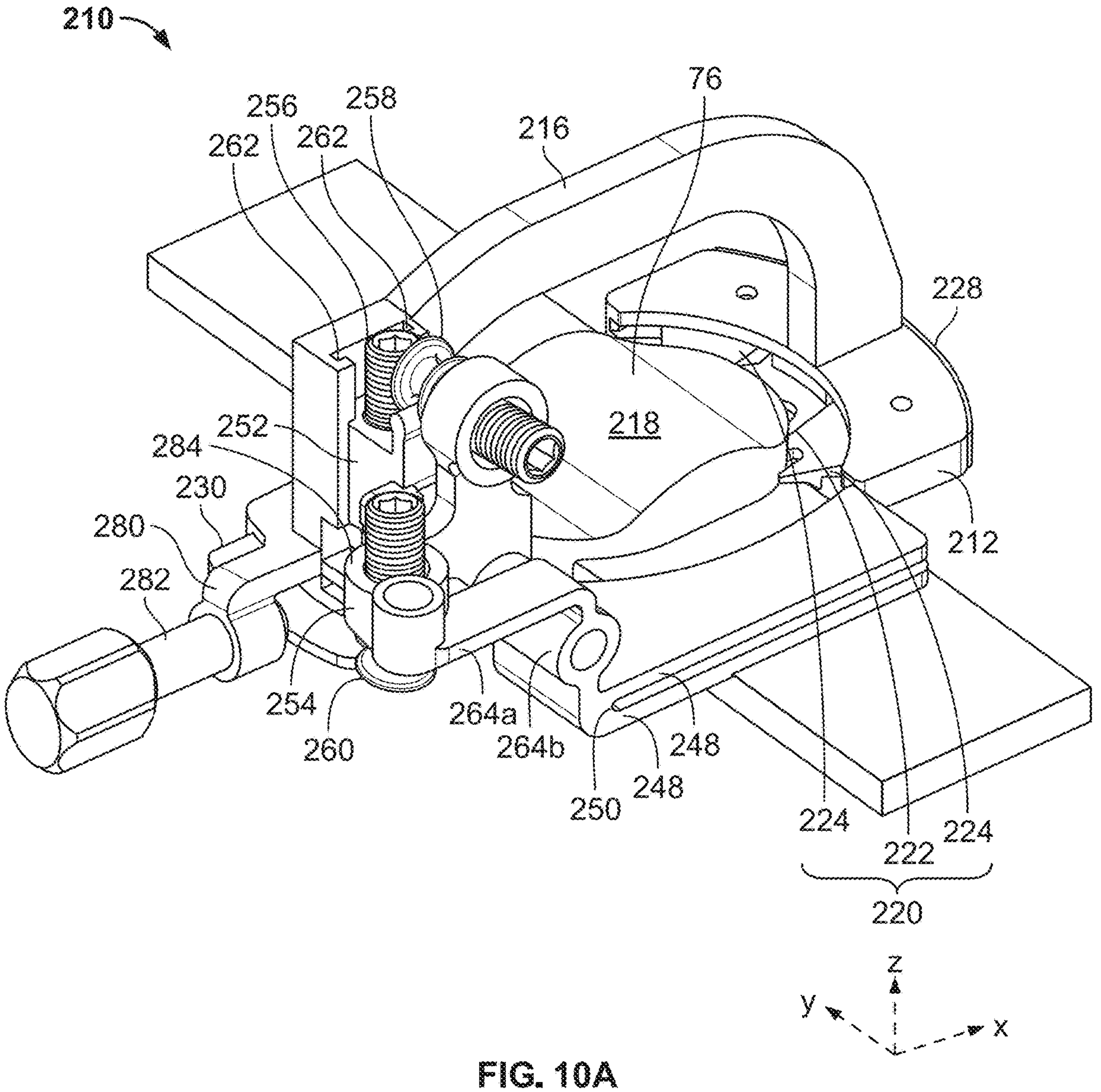
FIGS. 10A-10F illustrate stages in a process of using a guide according to another aspect.

FIG. 10A illustrates a guide 210 according to another arrangement. The guide 210 is generally similar to the guide 10 illustrated in FIGS. 1-8, with like numerals indicating like features (such as numerals 22 and 222 referring to a fixed mandible), except where specifically stated below. As such, not all numbered elements shown in FIGS. 10A-10F are specifically described herein. Further, the multiple differences between the guide 210 of FIG. 10A and the guide 10 of FIG. 1 may be implemented individually or in any combination.

The guide 210 includes two parallel arms 248 defining a cutting slot 250 therebetween. The two parallel arms 248 are both connected to the tube 264*b* and thus move together when adjusted in the same manner as described above with regard to the single arm 48 of the guide 10. The cutting slot 250 may therefore be used to guide a cutting instrument in generally the same manner as the planar surface 50 of the guide 10.

An actuator brace 280 extends backward from the bracket 216 along the longitudinal axis X and retains an actuator rod 282. The actuator rod 282 is disposed through a bore in the actuator brace 280 in a position aligning the actuator rod 282 parallel to the longitudinal axis X. The actuator rod 282 can be actuated to move longitudinally within the bore of the actuator brace 280 to bear on the second jaw 230. For example, the actuator rod 282 may be externally threaded to match internal threading of the bore of the actuator brace 280 and actuated by rotation, such as by manipulation of a knob such as that shown on the actuator rod 282 in the illustrated arrangement. The actuator brace 280 and actuator rod 282 thereby provide a mechanism for selectively tightening the second jaw 230 toward the fixed mandible 222 to engage a patella.

Figure 10B:
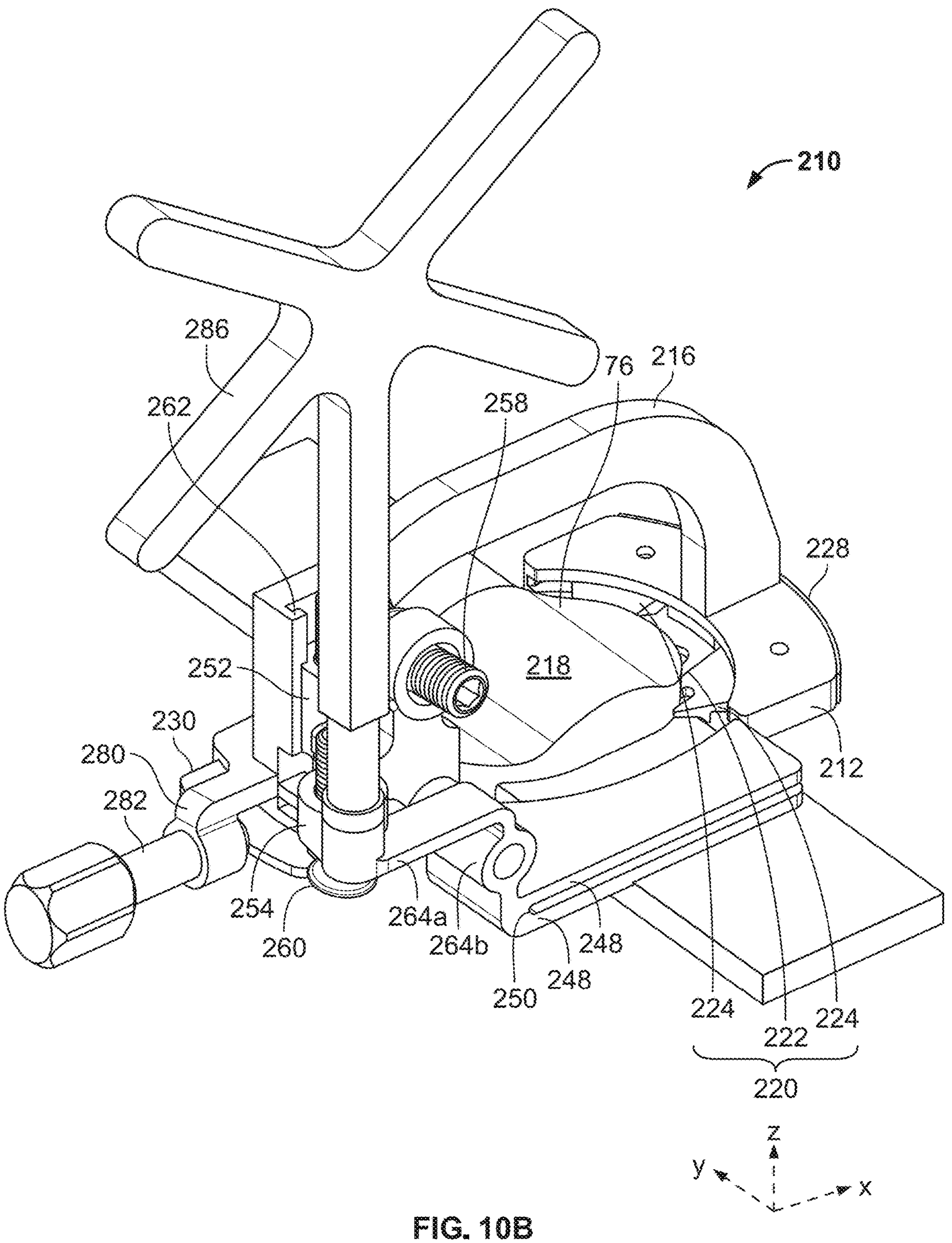
Figure 10C:
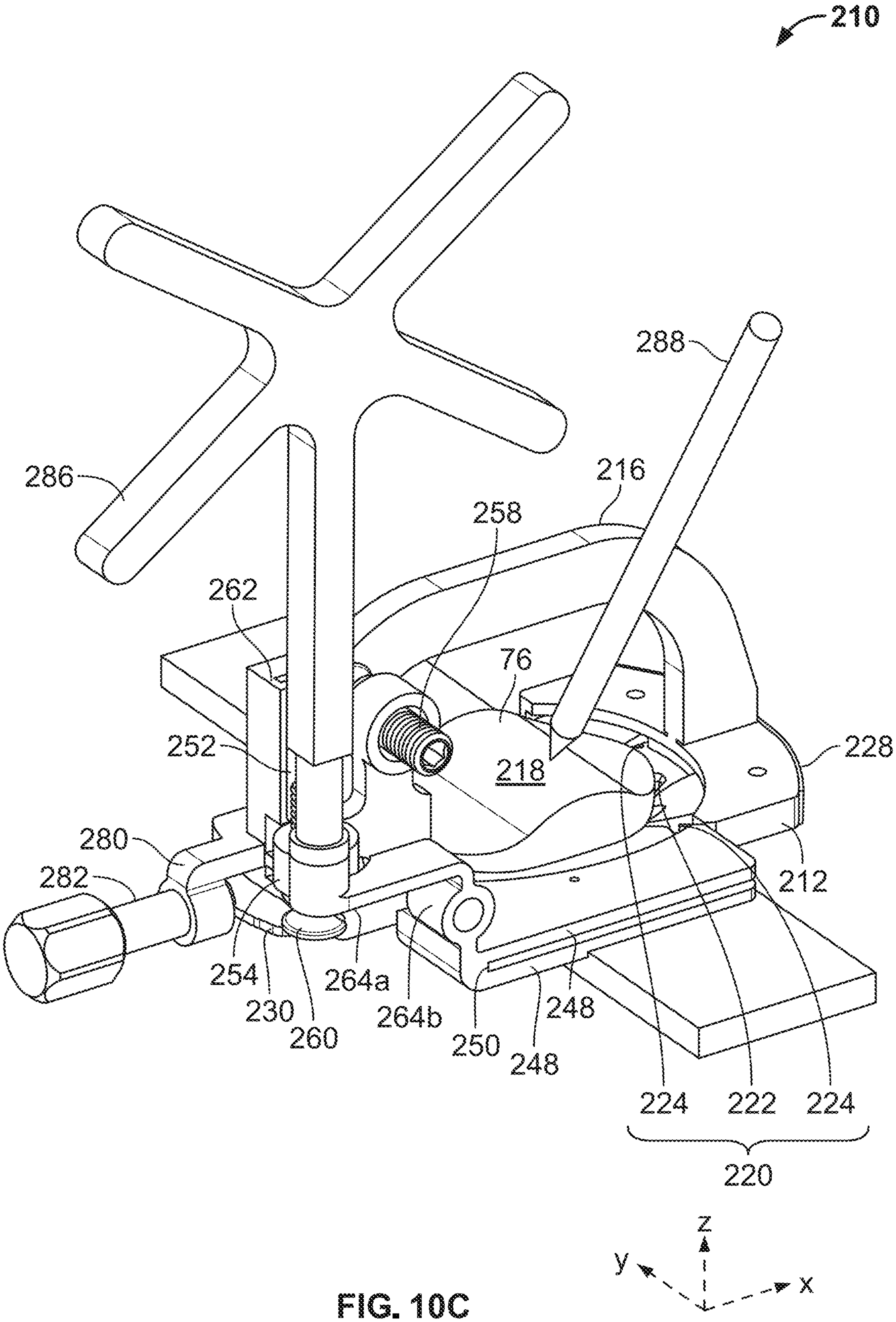
Figure 10D:
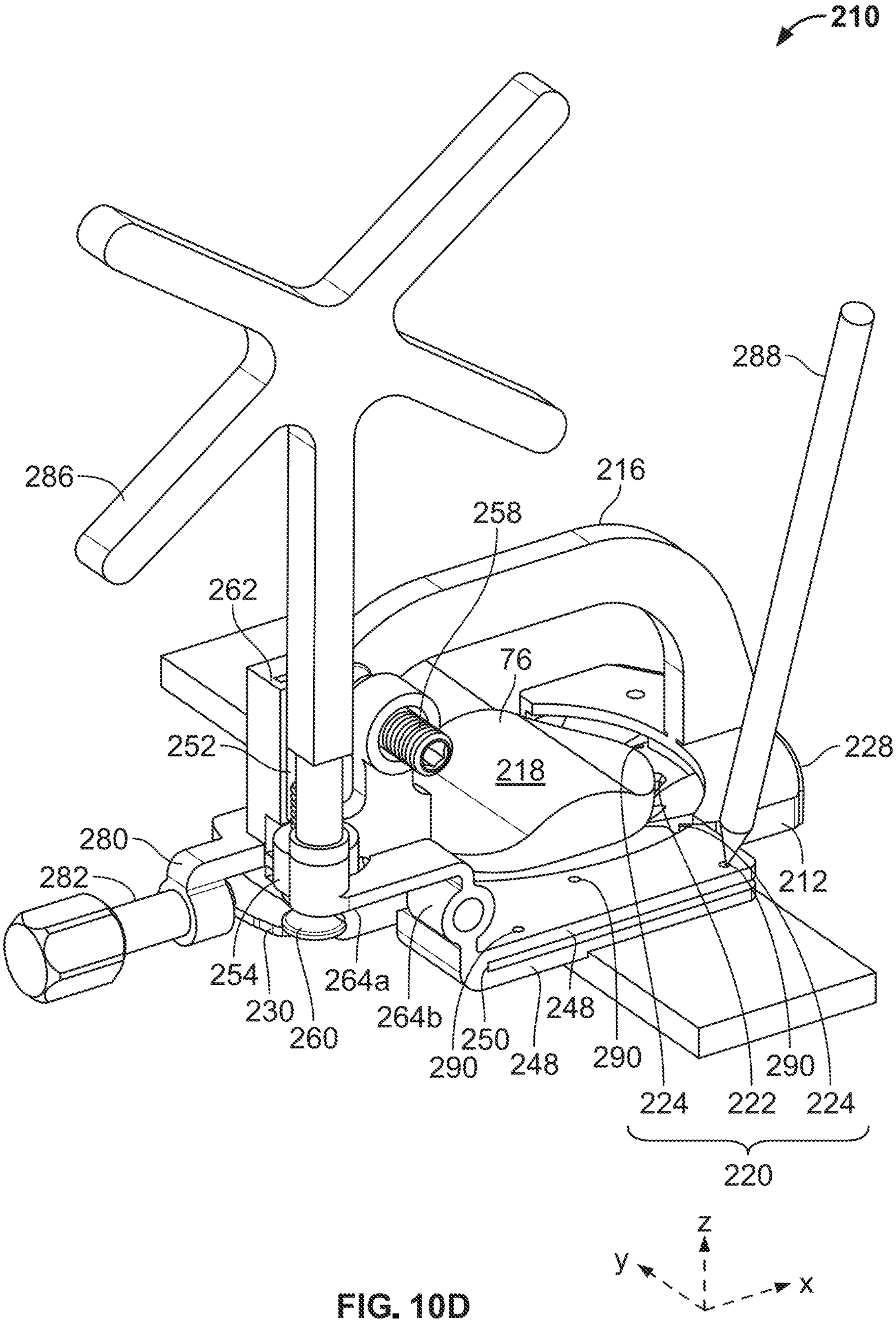
Figure 10E:
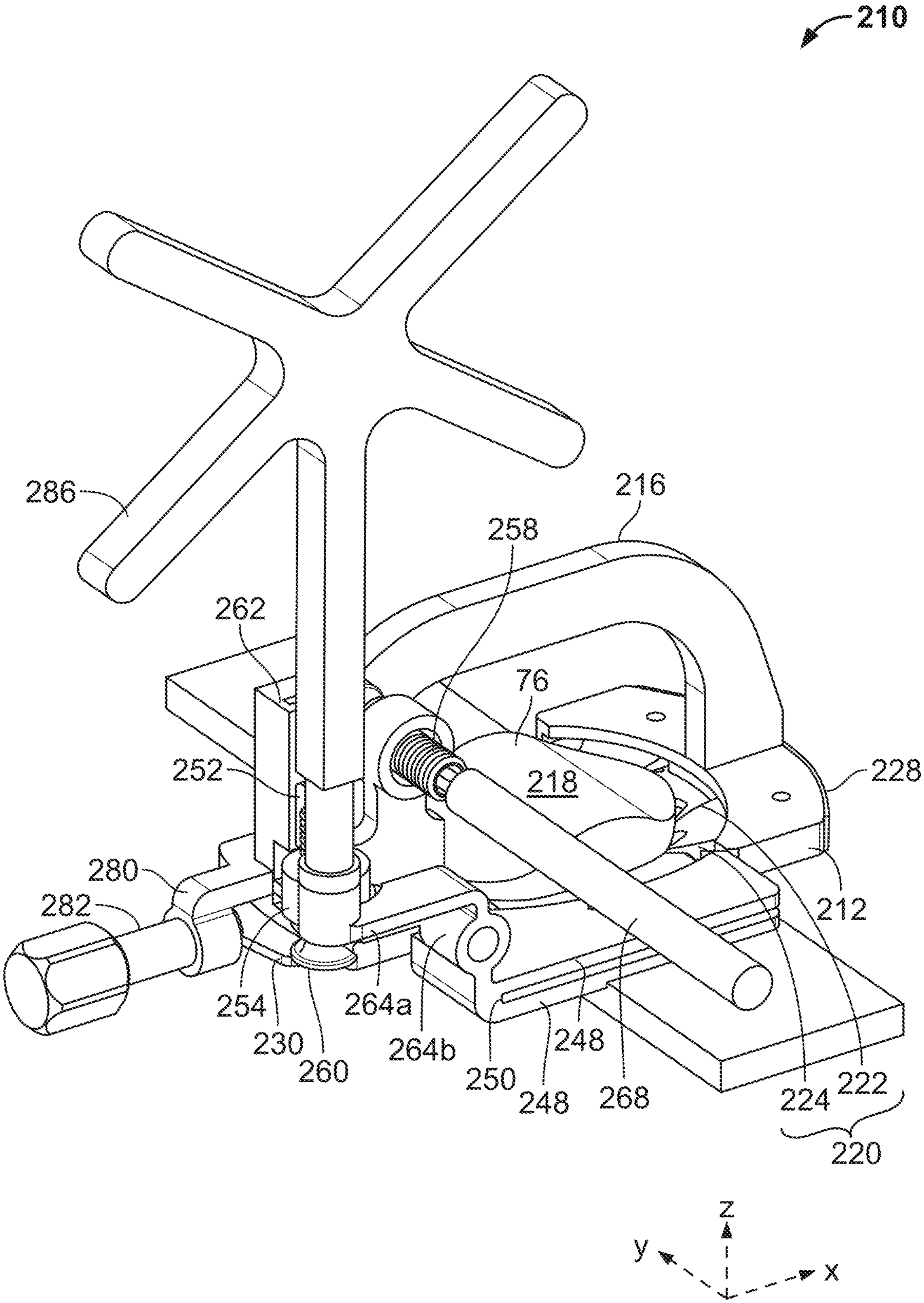
Figure 10F:
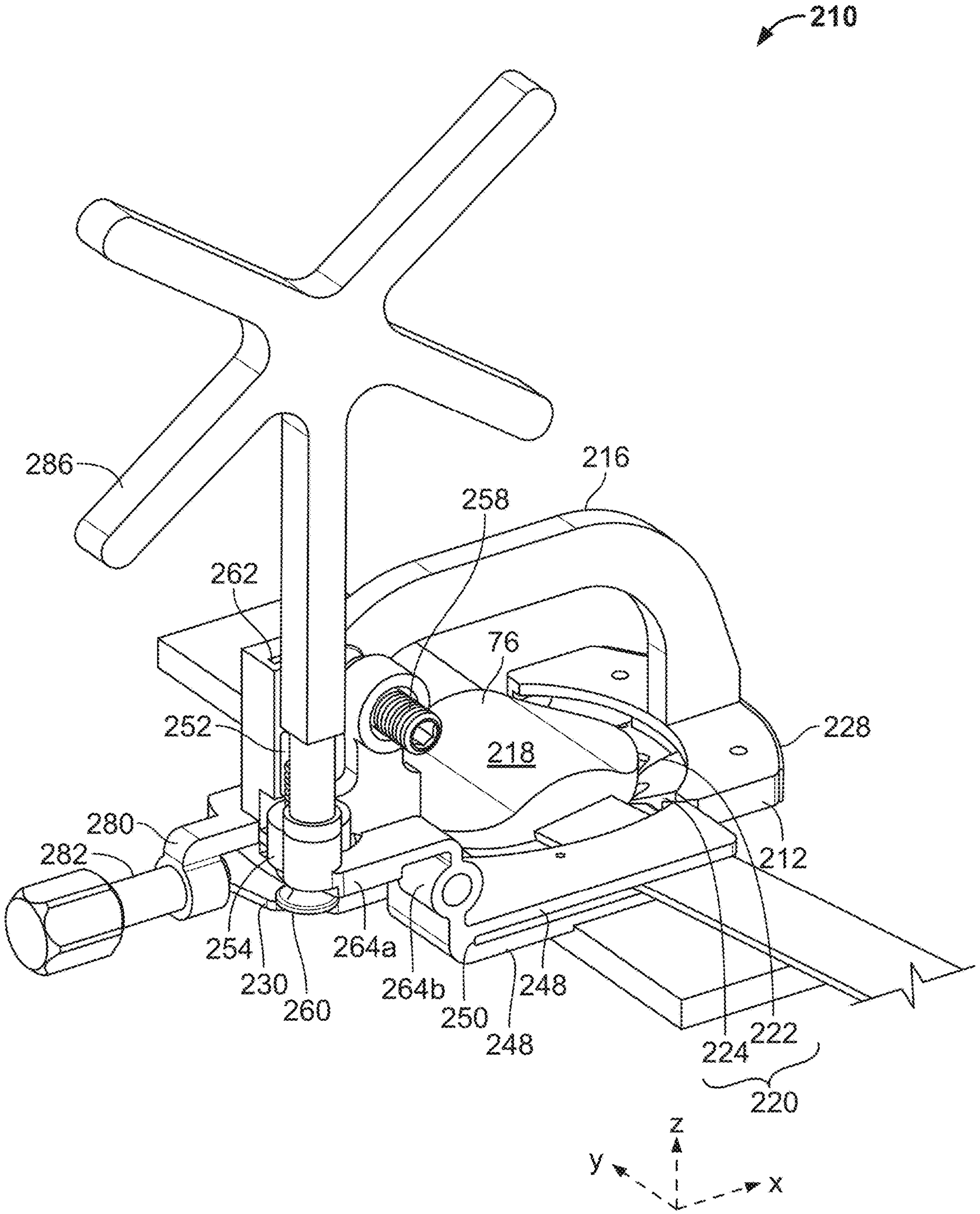

The tab 264*a* extending from the tube 264*b* includes a socket 284. Turning to FIG. 10B, the socket 284 can receive a peg of a computer recognizable orientation marker, being a navigation array 286 in the illustrated example, for use with a computer aided surgery system (CASS) before or after the jaws 220, 230 are engaged to the patella 76. Further, as shown in FIG. 10C, a probe 288 paired with the CASS can be used to map a topography of the patella 76. As shown in FIG. 10D, the probe 288 can also be contacted to three registration points 290 on one of the arms 248, which may be three predefined dimples 290. Because the tab 264*a* and the arms 248 are both connected at fixed relative positions to the tube 264*b*, the CASS can rely on the array 286 to determine the position and orientation of the arms 248 and cutting slot 250 relative to the patella 76. Thus, turning to FIG. 10E, the CASS may directly control the driver 268, or guide a surgeon in using the driver 268, to adjust the linkage generally as described above with regard to the guide 10 to put the arms 248 in a suitable position for cutting the patella 78 on an intended plane. Finally, as shown in FIG. 10F, the CASS or surgeon may guide the cutting tool 78 through the slot 250 to cut the patella 76.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patellar resection guide comprising:
- a frame including a first end and a second end opposed to the first end;
- a first jaw disposed at the first end of the frame;
- a second jaw disposed at the second end of the frame; and
- an arm movably connected to the frame such that a surface of the arm is adjustable from a first position aligned with a first plane to a second position aligned with a second plane non-parallel and non-perpendicular to the first plane.

2. The patellar resection guide of claim 1, wherein the arm further comprises a receiving surface configured to receive a portion of a computer recognizable orientation marker such that when the computer recognizable orientation marker is received on the receiving surface, a position and orientation of the arm is identifiable by a computer aided surgery system in communication with the computer recognizable orientation marker.

3. The patellar resection guide of claim 2, wherein the receiving surface is a socket.

4. The patellar resection guide of claim 1, wherein the surface of the arm further comprises a surface registration feature, a position and orientation of the surface registration feature being determinable when a computer recognizable orientation marker is attached to the arm and a navigation tool contacts the surface registration feature, the computer recognizable orientation marker and the navigation tool both being in communication with a computer aided surgery system.

5. The patellar resection guide of claim 4, wherein the surface registration feature is at least one surface irregularity.

6. The patellar resection guide of claim 4, wherein the surface registration feature is a first surface registration feature and the surface of the arm further comprises second and third surface registration features, the first, second and third surface registration features being coincident with the first plane when the arm is in the first position.

7. The patellar resection guide of claim 1, wherein the arm defines a cutting slot.

8. The patellar resection guide of claim 1, wherein the arm is rotatable relative to the frame about a first adjustment axis and a second adjustment axis different from the first adjustment axis.

9. The patellar resection guide of claim 8, wherein the arm is connected to the frame such that rotation of the arm about the second adjustment axis changes the first adjustment axis.

10. The patellar resection guide of claim 8, wherein the first jaw and the second jaw each include teeth, the teeth of the respective first and second jaws being coincident with a frame plane.

11. The patellar resection guide of claim 10, wherein the arm is rotatable about the second adjustment axis to a position at which the first adjustment axis extends parallel to the frame plane.

12. The patellar resection guide of claim 1, wherein the arm is configured to translate relative to the frame such that a planar surface of the arm becomes closer to or further from a gripping plane, the gripping plane passing through the first jaw and the second jaw.

13. A patellar resection system comprising:

the patellar resection guide of claim 1; and a computer recognizable orientation marker attached to the arm, the computer recognizable orientation marker and the arm being at a fixed position and orientation relative to each other, the computer recognizable orientation marker being configured to be in operative communication with a computer aided surgery system that detects a position and orientation of the computer recognizable orientation marker.

14. The patellar resection system of claim 13, further comprising:

the computer aided surgery system, wherein the computer aided surgery system includes a processor; and a navigation tool paired with the computer aided surgery system, wherein the processor of the computer aided surgery system is configured to:

receive patellar topography data of a patient when the navigation tool contacts a patella of the patient gripped by the first jaw and the second jaw;

receive arm location data when the navigation tool contacts a surface registration feature on the arm; and determine, based on the arm location data and the patellar topography data, a position and an orientation of the arm relative to the patella.

15. A patellar resection guide comprising:

a frame extending from a first end to a second end opposite the first end;

a first jaw disposed at the first end of the frame;

a second jaw disposed at the second end of the frame, a first plane passing through a portion of a first gripping edge of the first jaw and a portion of a second gripping edge of the second jaw; and an arm comprising a planar surface, the arm being movably connected to the frame so the planar surface is movable from a first position relative to the first plane to a second position relative to the first plane, the second position being different from the first position, wherein the planar surface is angulated transversely relative to the first plane in at least one of the first position or the second position.

16. The patellar resection guide of claim 15, wherein the arm further comprises a receiving surface configured to receive a portion of a computer recognizable orientation marker, the computer recognizable orientation marker being configured to detect a position and orientation of the planar surface.

17. The patellar resection guide of claim 16, wherein the receiving surface is a socket.

18. The patellar resection guide of claim 16, wherein the computer recognizable orientation marker and the arm are at a fixed position and orientation relative to each other.

19. The patellar resection guide of claim 15, wherein the arm includes one or more surface irregularities such that when the arm includes a computer recognizable orientation marker received thereon, a position and orientation of the planar surface is detectable when the one or more surface irregularities are contacted by a navigation tool.

20. A patellar resection guide comprising:

a frame extending from a first end to a second end opposite the first end;

a first jaw disposed at the first end of the frame;

a second jaw disposed at the second end of the frame, a first plane passing through a portion of a first gripping edge of the first jaw and a portion of a second gripping edge of the second jaw; and an arm including a planar surface and one or more surface irregularities, the arm being movably connected to the frame such that the planar surface is movable relative to the first plane with movement of the arm, wherein the arm is configured such that a navigation array is disposable thereon and a position and orientation of the planar surface relative to the first plane is identifiable when the navigation array is disposed on the arm and the one or more surface irregularities is contacted by a navigation tool.

* * * * *